United States Patent
Satelli et al.

(10) Patent No.: US 10,329,353 B2
(45) Date of Patent: Jun. 25, 2019

(54) SPECIFIC DETECTION TOOL FOR MESENCHYMAL AND EPITHELIAL-MESENCHYMAL TRANSFORMED CIRCULATING TUMOR CELLS

(71) Applicant: Board of Regents, The University of Texas System, Austin, TX (US)

(72) Inventors: Arun Satelli, Richmond, TX (US); Shulin Li, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 59 days.

(21) Appl. No.: 14/772,655

(22) PCT Filed: Mar. 5, 2014

(86) PCT No.: PCT/US2014/020615
§ 371 (c)(1),
(2) Date: Sep. 3, 2015

(87) PCT Pub. No.: WO2014/138183
PCT Pub. Date: Sep. 12, 2014

(65) Prior Publication Data
US 2016/0009812 A1    Jan. 14, 2016

Related U.S. Application Data

(60) Provisional application No. 61/772,973, filed on Mar. 5, 2013.

(51) Int. Cl.
| | | |
|---|---|---|
| *C07K 16/30* | (2006.01) | |
| *C07K 16/18* | (2006.01) | |
| *A61K 39/395* | (2006.01) | |
| *A61K 45/06* | (2006.01) | |
| *C07K 16/28* | (2006.01) | |
| *G01N 33/577* | (2006.01) | |
| *A61K 39/00* | (2006.01) | |

(52) U.S. Cl.
CPC ........ *C07K 16/30* (2013.01); *A61K 39/39558* (2013.01); *A61K 45/06* (2013.01); *C07K 16/18* (2013.01); *C07K 16/28* (2013.01); *C07K 16/3053* (2013.01); *G01N 33/577* (2013.01); *A61K 2039/505* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | |
|---|---|---|
| 7,670,604 B2 | 3/2010 | Georges et al. |
| 2005/0220797 A1 | 10/2005 | Chanh et al. |
| 2007/0202079 A1 * | 8/2007 | Yi .................. A61K 31/29 424/85.7 |
| 2007/0248539 A1 | 10/2007 | Glassy et al. |
| 2007/0265185 A1 | 11/2007 | Bouamrani et al. |
| 2009/0170123 A1 | 7/2009 | Donate et al. |
| 2010/0260667 A1 | 10/2010 | Georges et al. |

FOREIGN PATENT DOCUMENTS

| | | | |
|---|---|---|---|
| CN | 1871517 | 11/2006 | |
| EP | 1593691 | 11/2005 | |
| EP | 1598419 | 11/2005 | |
| EP | 2332984 | 6/2011 | |
| JP | 2005-040126 | 2/2005 | |
| JP | 2007-515924 | 6/2007 | |
| WO | WO 2003-065042 | 8/2003 | |
| WO | WO 2005/062058 | 7/2005 | |
| WO | WO 2006/108087 | 10/2006 | |
| WO | WO 2011/093927 | * 8/2011 | ............. G01N 33/53 |

OTHER PUBLICATIONS

Paterlini-Brechot et al. (Cancer Letters, 253: 180-208, 2007).*
Rafiq et al. (Journal of Clinical Investigation, 110(1): 71-79, 2002).*
Mariuzza (Annu. Rev. Biophys. Biophys. Chem., 16: 139-159, 1987).*
McCarthy et al. (J. Immunol. Methods, 251(1-2): 137-149, 2001).*
Bednarz et al., "BRCA1 loss pre-existing in small subpopulations of prostate cancer is associated with advanced disease and metastatic spread to lymph nodes and peripheral blood," *Clin Cancer Res.*, 16(13):3340-3348, 2010.
Bednarz-Knoll et al., "Clinical relevance and biology of circulating tumor cells," *Breast Cancer Research*, 13:228, 2011.
Ghazani et al., "Sensitive and direct detection of circulating tumor cells by multimarker μ-nuclear magnetic resonance," *Neoplasia*, 14:388-395, 2012.
Huet et al., "SC5 mAb represents a unique tool for the detection of extracellular vimentin as a specific marker of sézary cells," *The Journal of Immunology*, 176:652-659, 2006.
Ise et al., "Engulfment and clearance of apoptotic cells based on a GlcNAc-binding lectin-like property of surface vimentin," *Glycobiology*, 22(6):788-805, 2012.
Ise et al., "Vimentin and desmin possess GlcNAc-binding lectin-like properties on cell surfaces," *Glycobiology*, 20(7):843-864, 2010.
Kallergi et al., "Epithelial to mesenchymal transition markers expressed in circulating tumour cells of early and metastatic breast cancer patients," *Breast Cancer Research*, 13:R59, 2011.

(Continued)

*Primary Examiner* — Nelson B Moseley, II
(74) *Attorney, Agent, or Firm* — Parker Highlander PLLC

(57) ABSTRACT

The present invention includes the discovery of cell-surface vimentin as a novel biomarker to detect and isolate mesenchymal and epithelial-mesenchymal transformed circulating tumor cells from blood of cancer patients. In addition, an antibody specific for the detection of cell-surface vimentin on circulating tumor cells and the use the antibody to detect, enumerate, and isolate CTC are provided.

16 Claims, 34 Drawing Sheets
Specification includes a Sequence Listing.

(56) References Cited

OTHER PUBLICATIONS

Komura et al., "Dynamic behaviors of vimentin induced by interatction with GlcNAc molecules," *Glycobiology*, 22(12):1741-1759, 2012.
Koudelka et al., "Endothelial targeting of cowpea mosaic virus (CPMV) via surface vimentin," *PLoS Pathog.*, 5(5):e1000417, 2009.
Lecharpentier et al., "Detection of circulating tumour cells with a hybrid (epithelial/mesenchymal) phenotype in patients with metastatic non-small cell lung cancer," *British Journal of Cancer*, 105:1338-1341, 2011.
Mitra et al., "Cell-sruface Vimentin: a mislocalized protein for isolating csVimentin⁺CD133⁻ novel stem-like hepatocellular carcinoma cells expressing EMT markers," *Int. J. Cancer*, 137:491-496, 2015.
Mor-Vaknin et al., "Vimentin is secreted by activated macrophages," *Nat Cell Biol.*, 5(1):59-63, 2003.
Neal et al., "Capture of EpCAM-negative and vimetin-positive circulating cancer cells (CCCs) from blood of metastatic breast cancer patients using ApoStream," *J Clin Oncol*, 30(Suppl):e21029, Abstract from American Society of Clinical Oncology Annual Meeting, 2012.
PCT International Preliminary Report on Patentability issued in International Application No. PCT/US2014/020615, dated Sep. 8, 2015.
PCT International Search Report and Written Opinion issued in International Application No. PCT/US2014/020615, dated Jun. 2, 2014.
Raimondi et al., "Epithelial-mesenchymal transition and sternness features in circulating tumor cells from breast cancer patients," *Breast Cancer Res Treat.*, 130(2):449-455, 2011.
Satelli and Li, "Vimentin in cancer and its potential as a molecular target for cancer therapy," *Cell Mol Life Sci.*, 68(18):3033-3046, 2011.
Satelli et al., "Circulating tumor cell enumeration with a combination of epithelial cell adhesion molecule- and cell-surface vimentin-based methods for monitoring breast cancer therapeutic response," *Clinical Chemistry*, 61:259-266, 2015.
Satelli et al., "Epithelial-mesenchymal transitioned circulating tumor cells capture for detecting tumor progression," *Clinical Cancer Research*, 21(4):899-906, 2015.
Satelli et al., "Universal marker and detection tool for human sarcoma circulating tumor cells," *Cancer Res.*, 74(6):1645-1650,
Steinmetz et al., "Cowpea mosaic virus nanoparticles target surface vimentin on cancer cells," *Nanomedicine* (Lond)., 6(2):351-364, 2011.
Steinmetz et al., "Two domains of Vimentin are expressed on the surface of lymph node, bone and brain metastatic prostate cancer lines along with the putative stem cell marker proteins CD44 and CD133," *Cancers* (Basel)., 3(3):2870-2885, 2011.
Extended European Search Report and Search Opinion issued in European Application No. 14760783.2, dated Sep. 26, 2016.
Ortonne et al., "Significance of circulating T-cell clones in Sézary syndrome," *Blood*, 107:4030-4038, 2006.
Aotsuka et al., "Identification of a malignant cell associated antigen recognized by a human monoclonal antibody," *European Journal of Cancer and Clinical Oncology*, 24(5):829-838, 1988.
Office Action issued in European Application No. 14760783.2, dated Oct. 18, 2017.
Weidle et al., "Intracellular Proteins Displayed on the Surface of Tumor Cells as Targets for Therapeutic Intervention with Antibody-related Agents," *Cancer Genomics & Proteomics*, 8: 49-64, 2011.
Chazotte, "Labeling nuclear DNA using DAPI," *Cold Spring Har Protoc.*, pdb.prot5556, 2011.
Li et al., "Detection of circulating tumor cells from cryopreserved human sarcoma peripheral blood mononuclear cells," *Cancer Lett.*, 403:216-223, 2017.
Office Action issued in Japanese Application No. 2015-561585, dated Jan. 19, 2018, and English language translation thereof.
Jespers et al., "Guiding the selection of human antibodies from phage display repertoires to a single epitope of an antigen," *Bio/Technology*, 12:899-903, 1994 (Abstract only).
Office Action issued in Chinese Application No. 201480023572, dated Jul. 2, 2018, and English language translation thereof.

* cited by examiner

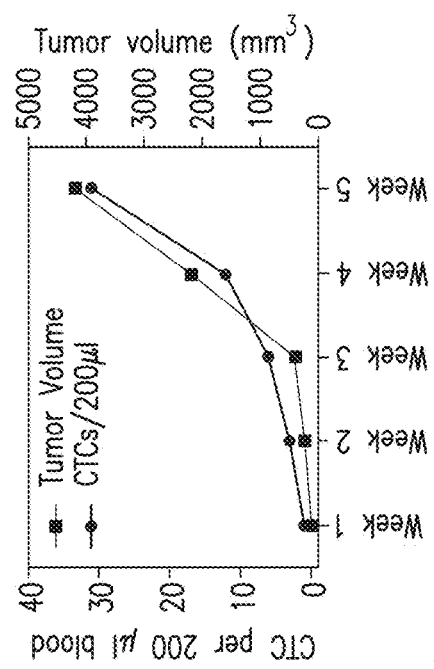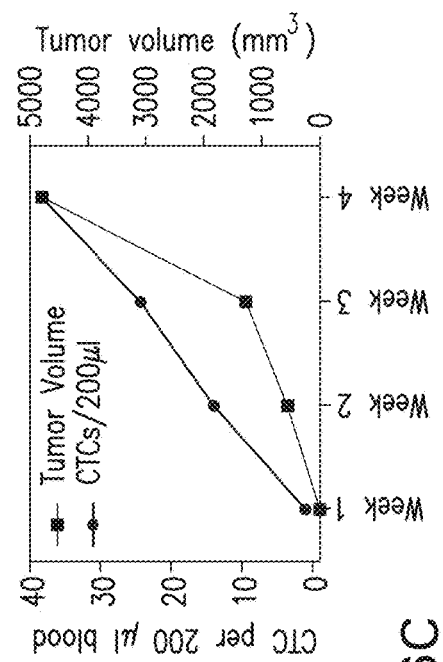
FIG.6B
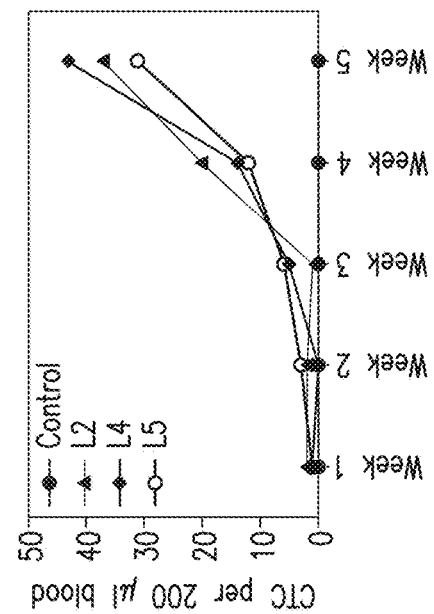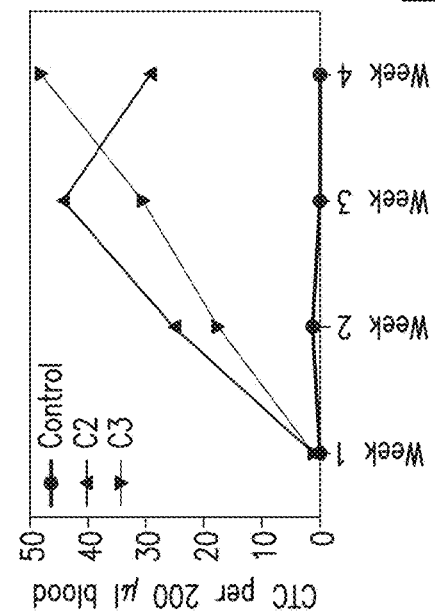
FIG.6C

SPECIFIC DETECTION TOOL FOR MESENCHYMAL AND EPITHELIAL-MESENCHYMAL TRANSFORMED CIRCULATING TUMOR CELLS

The present application is a national phase application under 35 U.S.C. § 371 of International Application No. PCT/US2014/020615, filed Mar. 5, 2014, which claims the priority benefit of U.S. provisional application No. 61/772,973, filed Mar. 5, 2013, the entire contents of which are incorporated herein by reference.

The invention was made with government support under Grant No. CA120295 awarded by the National Institutes of Health. The government has certain rights in the invention.

The sequence listing that is contained in the file names "UTFCP1208WO_ST25.txt", which is 3 KB (as measured in Microsoft Windows) and was created on Feb. 18, 2014, is filed herewith by electronic submission and is incorporated by reference herein.

BACKGROUND OF THE INVENTION

1. Field of the Invention

The present invention relates generally to the field of cancer biology. More particularly, it concerns the enumeration and isolation of circulating tumor cells to aid in early detection of tumors, metastases, and relapse.

2. Description of Related Art

Metastasis is the major cause for cancer-related deaths. Circulating tumor cells (CTC) are considered to be the seeds of metastasis and are defined as rare cells that detach themselves from the primary tumor into the blood stream and travel toward distant organs to colonize into metastases (Pantel and Brakenhoff, 2004). Although recent advances in the field of cancer therapy are able to contain the primary cancer from spreading, there is a need for a dependable biomarker for the early detection, diagnosis, and therapeutic monitoring of metastatic cancers. CTCs present in the peripheral blood of cancer patients are emerging as promising targets for early detection and monitoring therapeutic efficacy of anti-cancer drugs (Parkinson et al., 2012). At present, acceptable markers for detection of CTC include EpCAM and cytokeratins (Parkinson et al., 2012). However, these markers can detect only epithelial CTC, thereby excluding the epithelial-mesenchymal transformed (EMT) CTC that have lost expression of EpCAM (Sieuwerts et al., 2009) and any other non-epithelial CTC that originate from mesenchymal tumors, which constitute about 10% of adult and about 20% of pediatric cancer types (Mackall et al., 2002). This limitation of the current detection tools suggests a desperate need for novel tools that can fulfill these requirements.

SUMMARY OF THE INVENTION

The present invention, in some embodiments, provides a novel antibody for the detection of cell surface vimentin on circulating tumor cells. In one embodiment, the invention provides an isolated monoclonal antibody, wherein the antibody specifically binds to a vimentin polypeptide and wherein the antibody competes for binding of the polypeptide with an 84-1 monoclonal antibody. In certain aspects, a monoclonal antibody of the invention may bind to the same epitope as an 84-1 monoclonal antibody.

In one aspect, a monoclonal antibody of the present invention may comprise a first $V_H$ CDR at least 80% identical to $V_H$ CDR1 of 84-1 (SEQ ID NO: 3); a second $V_H$ CDR at least 80% identical to $V_H$ CDR2 of 84-1 (SEQ ID NO: 4); a third $V_H$ CDR at least 80% identical to $V_H$ CDR3 of 84-1 (SEQ ID NO: 5); a first $V_L$ CDR at least 80% identical to $V_L$ CDR1 of 84-1 (SEQ ID NO: 6); a second $V_L$ CDR at least 80% identical to $V_L$ CDR2 of 84-1 (SEQ ID NO: 7); and a third $V_L$ CDR at least 80% identical to $V_L$ CDR3 of 84-1 (SEQ ID NO: 8).

In another aspect, a monoclonal antibody of the present invention may comprise a first $V_H$ CDR is identical to SEQ ID NO: 3; a second $V_H$ CDR is identical to SEQ ID NO: 4; a third $V_H$ CDR is identical to SEQ ID NO: 5; a first $V_L$ CDR is identical to SEQ ID NO: 6; a second $V_L$ CDR is identical to SEQ ID NO: 7; and a third $V_L$ CDR is identical to SEQ ID NO: 8.

In yet another aspect, a monoclonal antibody of the present invention may comprise $V_H$ domain at least about 80% identical to the $V_H$ domain of 84-1 (SEQ ID NO: 1) and a $V_L$ domain at least about 80% identical to the $V_L$ domain of 84-1 (SEQ ID NO: 2). In a certain aspect, a monoclonal antibody of the invention may comprise a $V_H$ domain identical to the $V_H$ domain of 84-1 (SEQ ID NO: 1) and a $V_L$ domain identical to the $V_L$ domain of 84-1 (SEQ ID NO: 2). In another certain aspect, a monoclonal antibody of the invention may be the 84-1 antibody.

In some aspects, a monoclonal antibody disclosed herein may be recombinant. In some aspects, a monoclonal antibody of the embodiments may be an IgG, IgM, IgA or an antigen binding fragment thereof. In some aspects, a monoclonal antibody of the present invention may be a Fab', a F(ab')2, a F(ab')3, a monovalent scFv, a bivalent scFV, or a single domain antibody. In some aspects, a monoclonal antibody herein may be a human, humanized antibody or de-immunized antibody. In certain aspects, such a humanized or de-immunized antibody may comprise the foregoing CDRs on a human IgG (e.g., IgG1 or IgG2) backbone.

In certain aspects, a monoclonal antibody of the embodiments may be conjugated to an imaging agent, a chemotherapeutic agent, a toxin or a radionuclide. In certain aspects, a monoclonal antibody disclosed herein may be comprised in a pharmaceutically acceptable carrier.

In one embodiment, the present invention provides an isolated polynucleotide molecule comprising a nucleic acid sequence encoding a monoclonal antibody of the invention.

In one embodiment, the present invention provides a recombinant polypeptide comprising an antibody $V_H$ domain comprising CDRs 1-3 of the $V_H$ domain of 84-1 (SEQ ID NOs: 3, 4 and 5). In another embodiment, the present invention provides a recombinant polypeptide comprising an antibody $V_L$ domain comprising CDRs 1-3 of the $V_L$ domain of 84-1 (SEQ ID NOs: 6, 7 and 8). In another embodiment, the present invention provides an isolated polynucleotide molecule comprising a nucleic acid sequence encoding a polypeptide comprising an antibody $V_H$ domain comprising CDRs 1-3 of the $V_H$ domain of 84-1 (SEQ ID NOs: 3, 4 and 5) and/or an antibody $V_L$ domain comprising CDRs 1-3 of the $V_L$ domain of 84-1 (SEQ ID NOs: 6, 7 and 8).

In one embodiment, the present invention provides a host cell comprising one or more polynucleotide molecule(s) encoding a monoclonal antibody or recombinant protein of the embodiments. In certain aspects, the host cell may be a mammalian cell, a yeast cell, a bacterial cell, a ciliate cell or an insect cell.

In one embodiment, the present invention provides a method of manufacturing an antibody comprising expressing one or more polynucleotide molecule(s) encoding a $V_L$ and $V_H$ polypeptide chain of an antibody of the present invention in a cell and purifying the antibody from the cell.

In one embodiment, the present invention provides an isolated antibody, wherein the antibody comprises a first $V_H$ CDR at least 80% identical to $V_H$ CDR1 of 84-1 (SEQ ID NO: 3); a second $V_H$ CDR at least 80% identical to $V_H$ CDR2 of 84-1 (SEQ ID NO: 4); a third $V_H$ CDR at least 80% identical to $V_H$ CDR3 of 84-1 (SEQ ID NO: 5); a first $V_L$ CDR at least 80% identical to $V_L$ CDR1 of 84-1 (SEQ ID NO: 6); a second $V_L$ CDR at least 80% identical to $V_L$ CDR2 of 84-1 (SEQ ID NO: 7); and a third $V_L$ CDR at least 80% identical to $V_L$ CDR3 of 84-1 (SEQ ID NO: 8).

In one embodiment, the present invention provides a method of specifically detecting circulating tumor cells comprising (a) obtaining a blood sample from a patient, (b) incubating the sample with an antibody that binds to cell surface vimentin, and (c) detecting the antibody-bound cells. In certain aspects, the antibody that binds to cell surface vimentin may be an antibody disclosed herein. In some aspects, the antibody may be an antibody-like molecule, such as an aptamer, that binds to cell surface vimentin. In some aspects, detecting the antibody bound cells may comprise using flow cytometry, immunohistochemistry, fluorescence microscopy, radioimmunoassay, or ELISA.

In certain aspects, the method may further comprise depleting the sample of CD45-positive cells prior to incubating the sample with an antibody that binds to cell surface vimentin. In certain aspects, the method may further comprise increasing the level of cell surface vimentin expression by incubating the sample with a protein tyrosine phosphatase inhibitor. In some aspects, the protein tyrosine phosphatase inhibitor is sodium orthovanadate. In other aspects, the protein tyrosine phosphatase inhibitor may be dephostatin, mpV(pic), phenylarsine oxide, sodium stibogluconate, BAY U6751, a tyrosine phosphatase inhibitor cocktail (including sodium vanadate, sodium molybdate, sodium tartrate, and imidazole), or RK-682.

In certain aspects, the may be further defined as a method of isolating viable circulating tumor cells and further comprising separating the antibody-bound circulating tumor cell of (c) from the sample. In some aspects, separating may comprise immunomagnetic capture adhesion-based cell sorting, magnetic-activated cell sorting, or fluorescence-activated cell sorting (FACS). In certain aspects, the method may further comprise genotyping the isolated viable circulating tumor cells.

In certain aspects, the method may further comprise incubating the sample with EpCAM or cytokeratin antibodies. In certain aspects the method may further comprise quantifying the number of circulating tumor cells in the patient. In certain aspects, the blood sample is from a patient who has not been previously diagnosed with cancer, and the method is a method of early cancer detection. In another aspect, the blood sample is from a patient who is in remission, and the method is a method of detecting relapse. In some aspects, detecting at least about three circulating tumor cells per milliliter of blood is indicative of the patient having a tumor. In other aspects, detecting at least about one or at least about two circulating tumor cells per milliliter of blood is indicative of the patient having a tumor.

In certain aspects, the method may be a method of monitoring response to therapy in a cancer patient, wherein if the number of circulating tumor cells decreases over time, then the patient is said to have had a positive response to therapy. In certain aspects, the method may be a method of prognosis wherein detecting at least about five circulating tumor cells per milliliter of blood is indicative of the patient having a poor prognosis. In other aspects, the method may be a method of prognosis, wherein detecting at least about one, at least about two, at least about three, or at least about four circulating tumor cells per milliliter of blood is indicative of the patient having a poor prognosis.

In certain aspects, the patient may have an epithelial tumor. In other aspects, the patient may have a mesenchymal tumor. In certain aspects, the tumor may comprise a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In certain aspects, the tumor may comprise an osteosarcoma, angiosarcoma, rhabdosarcoma, leiomyosarcoma, Ewing sarcoma, glioblastoma, neuroblastoma, and leukemia.

In one embodiment, the present invention provides a method of treating a patient determined to have circulating tumor cells according to a method of the invention, the method comprising administering an effective amount of a conjugated antibody disclosed herein. In some aspects, the conjugated antibody may be comprised in a pharmaceutically acceptable composition.

In one aspect, the antibody may be administered systemically. In additional aspects, the antibody may be administered intravenously, intradermally, intratumorally, intramuscularly, intraperitoneally, subcutaneously, or locally. The method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy.

In further aspects, the method may further comprise administering a composition of the present invention more than one time to the subject, such as, for example, 1, 2, 3, 4, 5, 6, 7, 8, 9, 10, 15, 20 or more times.

In one embodiment, a composition is provided comprising an antibody of the present embodiments for use in the treatment of cancer in a subject. The subject may have been determined to have circulating tumor cells according to a method of the present embodiments. In some aspects, the subject may be a human. In some aspects, the subject may be a non-human mammal. In some aspects, the composition may be a pharmaceutically acceptable composition.

In certain aspects, the subject may have an epithelial tumor. In other aspects, the subject may have a mesenchymal tumor. In other aspects, the subject may have a metastatic tumor. In certain aspects, the tumor may comprise a breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. In certain aspects, the tumor may comprise an osteosarcoma, angiosarcoma, rhabdosarcoma, leiomyosarcoma, Ewing sarcoma, glioblastoma, neuroblastoma, and leukemia.

In some aspects, the composition may further comprise at least one other anti-cancer agent, such as a chemotherapeutic, radiotherapeutic, gene therapy, or a second immunotherapeutic agent. In some aspects, the composition may be formulated for systemic, intravenous, intradermal, intratumoral, intramuscular, intraperitoneal, subcutaneous, or local administration.

In one embodiment, provided herein is the use of an antibody of the present embodiments in the manufacture of a medicament for the treatment of a cancer in a subject, wherein the subject has been determined to comprise circulating tumor cells.

Certain embodiments are directed to an antibody or recombinant polypeptide composition comprising an isolated and/or recombinant antibody or polypeptide that specifically binds cell surface vimentin. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In still further aspects, an antibody or polypeptide of the embodiments comprises one or more amino acid segments of the any of the amino acid sequences disclosed herein. For example, the antibody or polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a cell surface vimentin-binding antibody as provided in Table 7.

In still further aspects, an antibody or polypeptide of the embodiments comprises an amino acid segment of the any of the amino acid sequences disclosed herein, wherein the segment begins at amino acid position 1, 2, 3, 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in any sequence provided herein and ends at amino acid position 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in the same provided sequence. In certain aspects the amino segment(s), or portions thereof, are selected from one of the amino acid sequences of a cell surface vimentin-binding antibody as provided in Table 7.

In yet further aspects, an antibody or polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of a cell surface vimentin-binding antibody (as provided in Table 7). For example, a polypeptide may comprise 1, 2 or 3 amino acid segment that are at least 80, 85, 90, 95, 96, 97, 98, 99, or 100% identical (or any range derivable therein) to CDRs 1, 2, and/or 3 the cell surface vimentin-binding antibody as provided in Table 7.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Isolation and characterization of 84-1, a cell surface vimentin (CSV) specific antibody.

FIG. 2: Methodology to isolate and enumerate CTCs using 84-1 mAb.

FIG. 3: Molecular characterization of isolated CTC.

FIG. 4.

FIG. 5.

FIG. 6: FIGS. 6B and C: Serial analysis of CTC in mice: Mice were implanted with LM8 (FIG. 6B) or CT-26 (FIG. 6C) cells. Approximately 200 µl of blood was obtained by sub-mandibular cheek bleeding method. Samples were obtained at approximately weekly intervals until mice were euthanized because of tumor burden. Left panels indicate CTCs enumerated weekly with normal mice as control. Representative data on the right panels of FIGS. 6B and C are shown from one mouse each with LM8 or CT-26 tumors, respectively. Data represented here is a plot of CTCs versus tumor volume that was obtained at weekly intervals.

FIG. 7.

DESCRIPTION OF ILLUSTRATIVE EMBODIMENTS

Figure 1A:
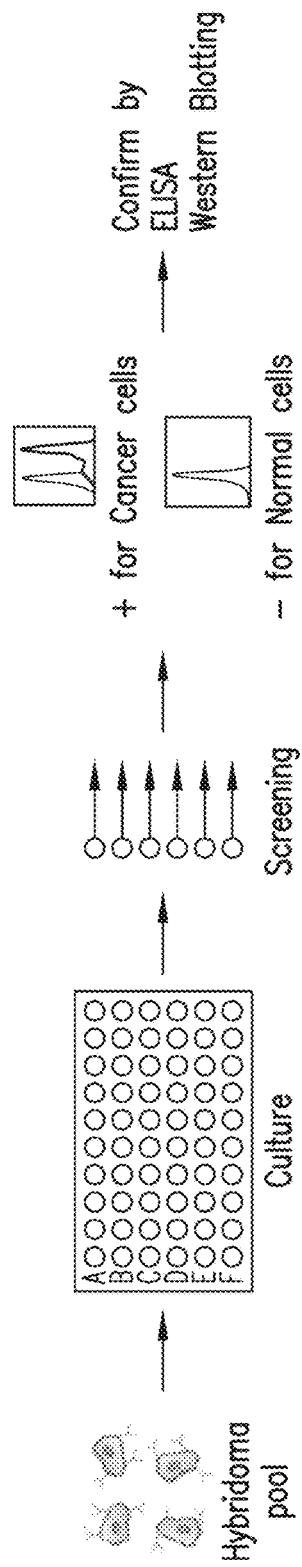
FIG. 1A: Schematic representation of screening antibodies for CSV specific antibody. Pools of monoclonal antibodies from different hybridoma supernatants were analyzed for CSV binding using flow cytometry and selecting for cancer specific binding. Selected antibody was characterized for vimentin binding using ELISA and western blotting.
Figure 1B:
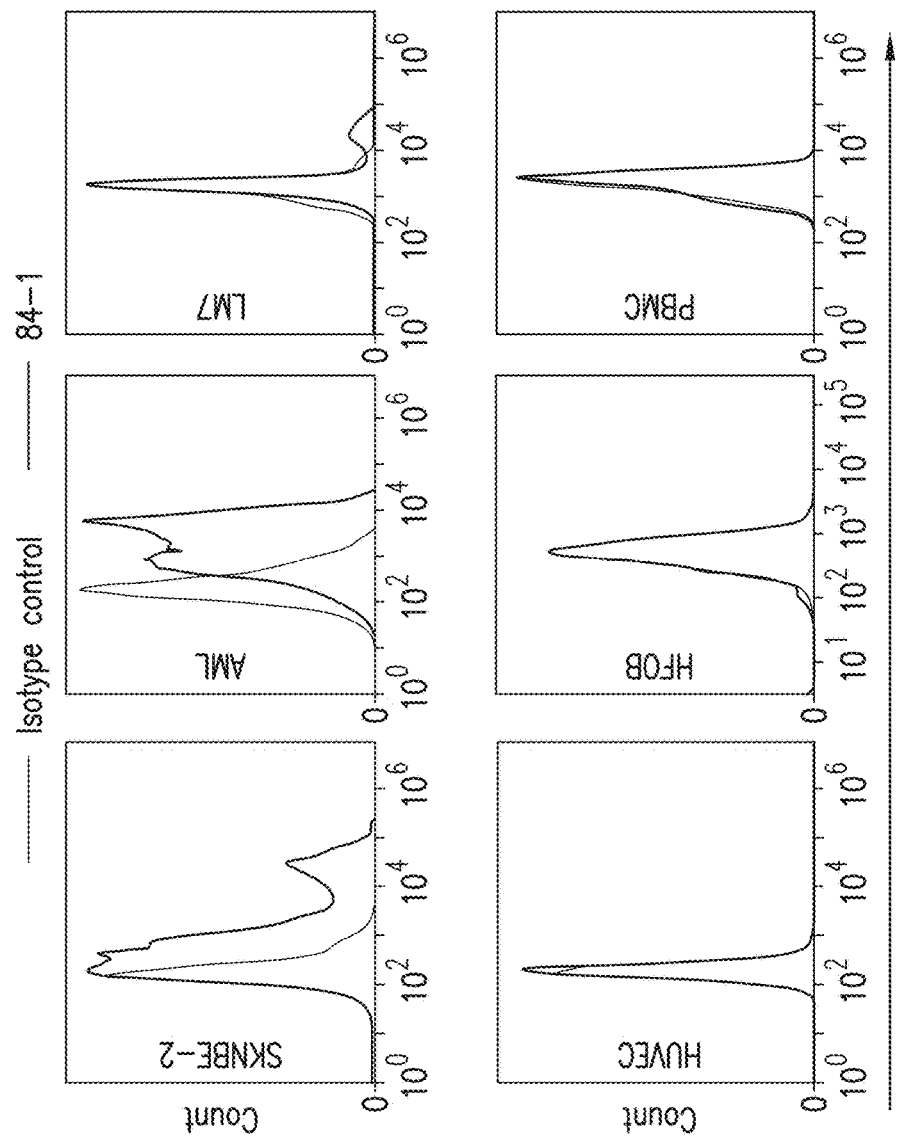
FIG. 1B: Immunological assessment of CSV expression in different non-epithelial normal and cancer cell lines using flow cytometry: CSV is detectable only in the cancer cell lines SKNBE-2 (neuroblastoma), AML cells isolated from patient blood and LM7 (osteosarcoma) cells, while the non-epithelial normal cells HUVEC, HFOB and PBMCs were negative for CSV expression. Isotype controls were used for negative controls.
Figure 1C:
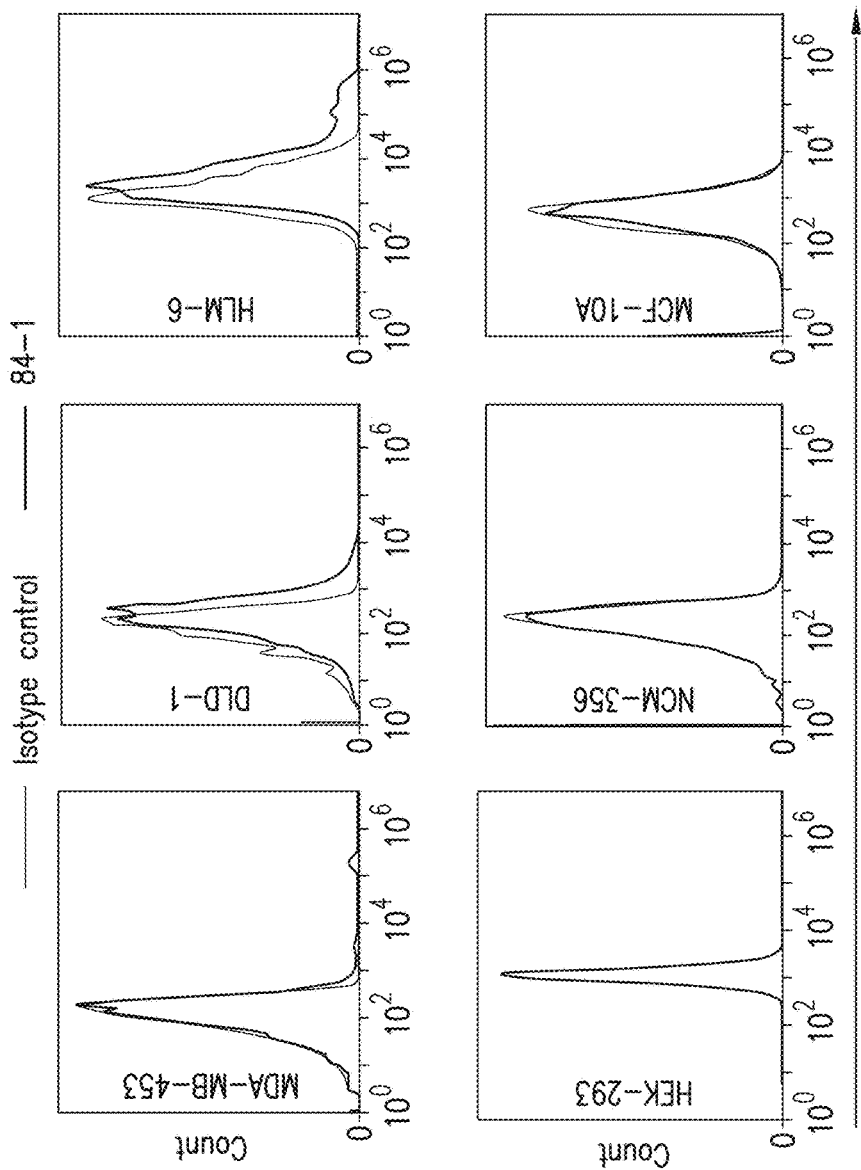
FIG. 1C: Immunological assessment of CSV in different epithelial normal and cancer cell lines using flow cytometry: CSV is detectable only in cancer cell lines MDA-MB-453 (breast cancer), DLD-1 (colon cancer) and HLM-6 (liver cancer), while normal epithelial cell lines HEK-293, NCM-356 and MCF-10A were negative for CSV expression.

Circulating tumor cell (CTC) detection in peripheral blood of cancer patients is emerging as novel tool in the early diagnosis and prognosis of several types of metastatic cancers. At present, CTC markers are limited to epithelial cancers and are unable to detect non-epithelial (i.e. mesenchymal) and epithelial-mesenchymal transformed (EMT) cancer cell types. Herein, the inventors report a novel cancer cell-surface vimentin (CSV) specific monoclonal antibody, 84-1, that shows high specificity and sensitivity (can detect 1 CTC from 1 million blood cells) toward non-epithelial and EMT CTC. This makes 84-1 an ideal tool for CTC detection and isolation. Further, the inventors also discovered a methodology to stimulate the cell-surface expression of vimentin on CTC using a phosphatase inhibitor, thus increasing the efficiency of detection and isolation. Detection and molecular characterization of CTCs is one of the fastest growing areas of translational cancer research. Utilizing the inventor's cell surface marker, the inventors can enumerate, isolate, and analyze CTCs to aid in the early detection of tumors, metastasis, and relapse. Likewise, 84-1 is a potential tool for monitoring and evaluating the efficiency of personalized therapy in cancer patients. Additionally, CTC isolated using the 84-1 antibody can be studied in detail, including molecular characterization to detect any mutations by genomic sequencing, which will contribute to the development of specific targeted therapies, an ultimate goal of personalized medicine.

The present invention includes: A) the discovery of cell-surface vimentin as a novel biomarker to detect and isolate mesenchymal and epithelial-mesenchymal transformed circulating tumor cells from blood of cancer patients; B) an antibody specific for the detection of cell-surface vimentin on circulating tumor cells; and C) the use of specific phosphatase inhibitors to enhance/stimulate the expression of cell-surface vimentin on CTC thereby enhancing the detection capacity of the antibody in part B).

I. Antibodies of the Invention

In certain embodiments, an antibody or a fragment thereof that binds to at least a portion of cell-surface vimentin and specifically detects vimentin on the surface of circulating tumor cells and its associated use in diagnosis and treatment of diseases are contemplated. As used herein, the term "antibody" is intended to refer broadly to any immunologic binding agent, such as IgG, IgM, IgA, IgD, and IgE as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-vimentin antibody is a monoclonal antibody or a humanized antibody. By known means and as described herein, polyclonal or monoclonal antibodies, antibody fragments, and binding domains and CDRs (including engineered forms of any of the foregoing) may be created that are specific to cell-surface vimentin, one or more of its respective epitopes, or conjugates of any of the foregoing, whether such antigens or epitopes are isolated from natural sources or are synthetic derivatives or variants of the natural compounds.

Examples of antibody fragments suitable for the present invention include, without limitation: (i) the Fab fragment, consisting of VL, VH, CL, and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (U.S. Patent App. Pub. 20050214860). Fv, scFv, or diabody molecules may be stabilized by the incorporation of disulphide bridges linking the VH and VL domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods. Addition tools that may be used to detect cell surface vimentin on CTC, including aptamers (e.g., generated from a DNA or RNA molecule), small peptides, and nanoparticles, are also contemplated.

Animals may be inoculated with an antigen, such as a 6-His-tagged soluble vimentin (NCBI Accession P08670, incorporate herein by reference), in order to produce antibodies specific for vimentin protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest. In the case of antibodies to vimentin, selectivity for detecting cell surface vimentin can be determined by assaying differential binding to cells that either do or do not express vimentin on their surface.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a vimentin antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881,557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in: Marks (1992); Stemmer (1994); Gram et al. (1992); Barbas et al. (1994); and Schier et al. (1996).

It is fully expected that antibodies to cell surface vimentin will have the ability to bind to CTC regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds cell surface vimentin.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against cell surface vimentin, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

II. Circulating Tumor Cells

CTCs may be detected in any suitable sample type. As used herein, the term "sample" refers to any sample suitable for the methods provided by the present invention. The sample may be any sample that includes CTCs suitable for detection. Sources of samples include whole blood, bone marrow, pleural fluid, peritoneal fluid, central spinal fluid, urine, saliva and bronchial washes. In one aspect, the sample is a blood sample, including, for example, whole blood or any fraction or component thereof. A blood sample, suitable for use with the present invention may be extracted from any source known that includes blood cells or components thereof, such as venous, arterial, peripheral, tissue, cord, and the like. For example, a sample may be obtained and processed using well known and routine clinical methods (e.g., procedures for drawing and processing whole blood). In one aspect, an exemplary sample may be peripheral blood drawn from a subject with cancer.

The term "cancer" as used herein, includes a variety of cancer types which are well known in the art, including but not limited to, dysplasias, hyperplasias, solid tumors and hematopoietic cancers. Many types of cancers are known to metastasize and shed circulating tumor cells or be metastatic, for example, a secondary cancer resulting from a primary cancer that has metastasized. Additional cancers may include, but are not limited to, the following organs or systems: brain, cardiac, lung, gastrointestinal, genitourinary tract, liver, bone, nervous system, gynecological, hematologic, skin, breast, and adrenal glands. Additional types of cancer cells include gliomas (Schwannoma, glioblastoma, astrocytoma), neuroblastoma, pheochromocytoma, paraganlioma, meningioma, adrenalcortical carcinoma, medulloblastoma, rhabdomyoscarcoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia; and skin cancers including malignant melanoma, basal cell carcinoma, squamous cell carcinoma, Karposi's sarcoma, moles dysplastic nevi, lipoma, angioma, dermatofibroma, keloids, sarcomas, such as fibrosarcoma or hemangiosarcoma, and melanoma.

The total number of detected CTCs included in a CTC population is dependent, in part, on the initial sample volume. In various aspects, detection of CTCs in a wide range of initial sample volumes is sufficient to produce a detected number of CTCs capable of providing clinically significant results. As such, the initial sample volume may be less than about 25 µl, 50 µl, 75 µl, 100 µl, 125 µl, 150 µl, 175 µl, 200 µl, 225 µl, 250 µl, 300 µl, 400 µl, 500 µl, 750 µl, 1 ml, 2 ml, 3 ml, 4 ml, 5 ml, 6 ml, 7 ml, 8 ml, 9 ml or greater than about 10 ml. In an exemplary aspect, the initial sample volume is between about 100 and 200 µl. In another exemplary aspect, a sample processed as described herein includes greater than about 1, 2, 5, 7, 10, 15, 20, 30, 40, 50, 100, 200, 300, 400, 500, 600, 700, 800, 900, or even 1000 revealed CTCs.

As used herein, analysis includes any method that allows direct or indirect visualization of CTCs and may be in vivo or ex vivo. For example, analysis may include, but not limited to, ex vivo microscopic or cytometric detection and visualization of cells bound to a solid substrate, flow cytometry, fluorescent imaging, and the like. In an exemplary aspect, CTCs are detected using antibodies directed to cell surface vimentin and subsequently bound to a solid substrate and visualized using microscopic or cytometric detection.

In another embodiment, the CTCs are captured by techniques commonly used to enrich a sample for CTCs, for example those involving immunospecific interactions, such as immunomagnetic capture. Immunomagnetic capture, also known as immunomagnetic cell separation, typically involves attaching antibodies directed to proteins found on a particular cell type to small paramagnetic beads. When the antibody-coated beads are mixed with a sample, such as blood, they attach to and surround the particular cell. The sample is then placed in a strong magnetic field, causing the beads to pellet to one side. After removing the blood, captured cells are retained with the beads. Many variations of this general method are well known in the art and suitable for use to isolate CTCs.

Detection, isolation, and characterization of CTCs, using the methods of the invention, is useful in assessing cancer prognosis and in monitoring therapeutic efficacy for early detection of treatment failure that may lead to disease relapse. In addition, CTC analysis according to the invention enables the detection of early relapse in presymptomatic patients who have completed a course of therapy. This is possible because the presence of CTCs has been associated and/or correlated with tumor progression and spread, poor response to therapy, relapse of disease, and/or decreased survival over a period of time. Thus, enumeration and characterization of CTCs provides methods to stratify patients for baseline characteristics that predict initial risk and subsequent risk based upon response to therapy.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Accordingly, in another embodiment, the invention provides a method for diagnosing or prognosing cancer in a subject. CTCs isolated according to the methods disclosed herein may be analyzed to diagnose or prognose cancer in the subject. As such, the methods of the present invention may be used, for example, to evaluate cancer patients and those at risk for cancer. In any of the methods of diagnosis or prognosis described herein, either the presence or the absence of one or more indicators of cancer, such as, a cancer cell, or of any other disorder, may be used to generate a diagnosis or prognosis.

In one aspect, a blood sample is drawn from the patient and CTCs are detected as described herein. Using the method of the invention, the number of CTCs in the blood sample is determined and the CTCs may be subsequently analyzed. For example, the cells may be labeled with one or more antibodies that bind to cell surface vimentin, cytokeratin, or EpCAM, and the antibodies may have a covalently bound fluorescent label. Analysis may then be performed to determine the number and characterization of CTCs in the sample, and from this measurement, the number of CTCs present in the initial blood sample may be determined. The number of CTCs may be determined by cytometric or microscopic techniques to visually quantify and characterize the CTCs.

In various aspects, analysis of a subject's CTC number and characterization may be made over a particular time course in various intervals to assess a subject's progression and pathology. For example, analysis may be performed at regular intervals such as one day, two days, three days, one week, two weeks, one month, two months, three months, six months, or one year, in order to track the level and characterization of CTC as a function of time. In the case of existing cancer patients, this provides a useful indication of the progression of the disease and assists medical practitioners in making appropriate therapeutic choices based on the increase, decrease, or lack of change in CTC. Any increase, be it 2-fold, 5-fold, 10-fold or higher, in CTCs over time decreases the patient's prognosis and is an early indicator that the patient should change therapy. Similarly, any increase, be it 2-fold, 5-fold, 10-fold or higher, indicates that a patient should undergo further testing such as imaging to further assess prognosis and response to therapy. Any decrease, be it 2-fold, 5-fold, 10-fold or higher, in CTCs over time shows disease stabilization and a patient's response to therapy, and is an indicator to not change therapy. For those at risk of cancer, a sudden increase in the number of CTC detected may provide an early warning that the patient has developed a tumor thus providing an early diagnosis. In one embodiment, the detection of CTCs increases the staging of the cancer.

In any of the methods provided herein, additional analysis may also be performed to characterize CTC to provide additional clinical assessment. For example, in addition to image analysis and bulk number measurements, PCR techniques may be employed, such as multiplexing with primers specific for particular cancer markers to obtain information such as the type of tumor from which the CTCs originated, metastatic state, and degree of malignancy. Additionally, cell size, DNA or RNA analysis, proteome analysis, or metabolome analysis may be performed as a means of assessing additional information regarding characterization of the patient's cancer.

For example, the additional analysis may provide data sufficient to make determinations of responsiveness of a subject to a particular therapeutic regime, or for determining the effectiveness of a candidate agent in the treatment of cancer. Accordingly, the present invention provides a method of determining responsiveness of a subject to a particular therapeutic regime or determining the effectiveness of a candidate agent in the treatment of cancer by detecting/isolating CTCs of the subject as described herein and analyzing said CTCs. For example, once a drug treatment is administered to a patient, it is possible to determine the efficacy of the drug treatment using the methods of the invention. For example, a sample taken from the patient before the drug treatment, as well as one or more cellular samples taken from the patient concurrently with or subsequent to the drug treatment, may be processed using the methods of the invention. By comparing the results of the analysis of each processed sample, one may determine the efficacy of the drug treatment or the responsiveness of the patient to the agent. In this manner, early identification may be made of failed compounds or early validation may be made of promising compounds.

III. Treatment of Diseases

Certain aspects of the present invention can be used to prevent or treat a disease or disorder associated with circulating tumor cells. The metastatic potential of CRC may be reduced by any suitable drugs to prevent CTC growth and colonization of tissues. Preferably, such substances would comprise an anti-cell surface vimentin antibody.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that inhibits CTC growth and colonization of tissues.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

A. Pharmaceutical Preparations

Where clinical application of a therapeutic composition containing an anti-cell surface vimentin antibody is undertaken, it will generally be beneficial to prepare a pharmaceutical or therapeutic composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters. A pharmaceutically acceptable carrier is particularly formulated for administration to a human, although in certain embodiments it may be desirable to use a pharmaceutically acceptable carrier that is formulated for administration to a non-human animal but that would not be acceptable (e.g., due to governmental regulations) for administration to a human. Except insofar as any conventional carrier is incompatible with the active ingredient, its use in the therapeutic or pharmaceutical compositions is contemplated.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present invention administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form.

Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

B. Combination Treatments

In certain embodiments, the compositions and methods of the present invention involve an antibody or an antibody fragment against cell surface vimentin to selectively bind CTC, in combination with a second or additional therapy. Such therapy can be applied in the treatment of any disease that is associated with CTC.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a CTC and/or the prevention of metastasis. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

An anti-cell surface vimentin antibody may be administered before, during, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below an antibody therapy is "A" and an anti-cancer therapy is "B":

| | | | | | | |
|---|---|---|---|---|---|---|
| A/B/A | B/A/B | B/B/A | A/A/B | A/B/B | B/A/A | A/B/B/B B/A/B/B |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Cell Lines.

DLD-1, GEO, and HUVEC cells were obtained from Dr. Lee Ellis (MD Anderson Cancer Center). LM7, SAOS-2, K7, K7M3, LM-8, and DUNN cells were kindly provided by Dr. Eugenie S Kleinerman (MD Anderson Cancer Center). HOS, MG-263, OS-D, OS-O, and OS-25 cells were kindly provided by Dr. Dennis Hughes (MD Anderson Cancer Center). SNU398, HEP3B, and SNU 449 cells were kindly provided by Dr. Lopa Mishra (MD Anderson Cancer Center). SKNAS, SKNBE2, SK-N-SH, NGP, CHP134, SH-SY5Y, LAN5, and KCN cells were kindly provided by Dr. Patrick Zweidler-McKay (MD Anderson Cancer Center). All other cell lines used in this study were obtained from American Type Culture Collection (ATCC) (Manassas, Va., USA). Primary cell cultures from Osteosarcoma patients were kindly provided by Dr. Dina Lev (MD Anderson Cancer Center). All cell lines were grown according to ATCC recommendations. Cell lines with no particular recommendations were grown in DMEM-F12 (Sigma Aldrich) with 10% fetal bovine serum (FBS) (Gibco, Invitrogen), 1% L-glutamine (Gibco, Invitrogen), and 0.1% penicillin/streptomycin (Gibco, Invitrogen). All cells were maintained at 37° C. in a 5% $CO_2$ incubator unless until specified. Primary cultures obtained from human colon, liver, lung, and bone cancers were cultured in DMEM/F-12 medium with 10% heat inactivated FBS, 1% L-glutamine, 100 µg/mL Primocin (Invivogen), and 0.1% penicillin/streptomycin.

CTCs isolated using the 84-1 antibody were cultured on fibronectin-coated plates (Thermo Fisher) in DMEM/F-12 medium with 10% heat-inactivated serum (Invitrogen) and supplementation of growth factors. CTCs isolated from Osteosarcoma patients were cultured with supplementation of 10 ng/mL of Human epidermal growth factor (hEGF) (Cell Signaling) and insulin growth factor (hIGF) (R&D Systems). CTCs isolated from colon cancer and liver patients were cultured with supplementation of 10 ng/mL of human EGF, IGF, and basic fibroblast growth factor (hFGF2). CTCs isolated from canine and mouse blood were cultured in the above-mentioned media with epidermal, insulin, and fibroblast growth factors (Cell Signaling). Media was changed once every four days. All cells were maintained at 37° C. in a 5% $CO_2$ incubator.

Geltrex Thin Layer Method.

HPC-1 cells were grown on Geltrex Reduced Growth Factor Basement Membrane Matrix (Invitrogen), which is a soluble form of basement membrane purified from Engelbreth-Holm-Swarm tumor that gels at 37° C. forming a reconstituted basement membrane that provides the matrix for the culture of cells. Major components of the Geltrex include various growth factors and laminin, collagen IV, entactin. As per manufacturer recommendation, Geltrex was thawed on ice and 100 µL of Geltrex was used for coating the Lab Tek chamber slides (Thermo) an hour before plating the cells. Later, 1000 HPC-1 cells in 100 µL cold serum-free DMEM/F-12 medium with 2% Geltrex were plated on the chamber slides with thin gel coating. The cells were grown at 37° C. in humidified atmosphere of 5% $CO_2$ in air and observed through microscope for the formation of spheres.

Blood Collection and Processing.

For mouse samples, blood was collected from mice using sub-mandibular cheek bleeding method and at a given time 200 µL of the blood was collected in an EDTA tube (Fisher) during the weekly follow up studies. At the end of the study, at least 800 µL of blood was collected using the left cardiac ventricle puncture method. Blood collected was then subjected to RBC Lysis using RBC Lysis buffer (eBioscience), as per the manufacturer's recommendation. Cells were then washed in PBS and used for further analysis.

Human blood samples for CTC analysis were obtained after informed consent, per IRB protocol at MD Anderson Cancer Center. A maximum of 8 mL of blood were obtained at any given blood draw, using CPT Vacutainer (BD Bioscience). Healthy blood samples were obtained from Gulf Coast Blood Center. Single nucleated cells were isolated as per the manufacturer's recommendation. Cells were then washed in PBS and used for further analysis.

Blood samples from canine were obtained from Gulf Coast Veterinary clinic. Privately owned dogs that were referred to the Gulf Coast Veterinary clinic were selected for the study. Apart from having histologically confirmed neoplastic disease, inclusion criteria included the absence of overt heart, renal, or other life-threatening illness. Dogs were staged by obtaining a thorough anamnesis, physical examination, complete blood cell count, serum biochemistry profile, urinalysis, electrocardiogram, thoracic radiographs (three-view metastasis check), and abdominal ultrasound if indicated. For confirmation of tumor type, excision biopsies from the primary tumor were obtained surgically under anesthesia and were placed in 10% neutral-buffered formalin. After being fixed, tissue was cut-in, paraffin embedded, sectioned, adhered to slides, stained with hematoxylin and eosin, cover-slipped, and evaluated by boarded veterinary pathologists.

Antibody Production.

Recombinant human vimentin (rhVim) with 6-His (R&D Systems) was used as an antigen for antibody production. Anti-vimentin titer was determined using ELISA assay. Briefly, rhVim was used as solid antigen in ELISA. Serum at serial two-fold dilutions was incubated for 2 h in ELISA wells coated with rhVim. After washes, and incubation with peroxidase-coupled anti-mouse IgG antibody, a color reaction was performed and analyzed with ortho-phenylenediamine (OPD). Antibodies that showed higher O.D. at lower dilutions were considered for further screening. Antibodies selected for screening were incubated with osteosarcoma cell lines with and without vimentin on the cell surface. Antibodies that have very high affinity for CSV were selected and analyzed further. 84-1 was the best clone available to detect cell surface vimentin with high affinity and sensitivity. This antibody was then further characterized for vimentin binding by ELISA, western blotting, immunoprecipitation, immunocytochemistry, and immunohistochemistry. Antibody 12-1 was also characterized for detection and isolation of CTC.

84-1 Positive Cell Selection.

CD45 positive cells were first depleted using the EasySep™ Human CD45 Depletion Kit with manufacturer's recommendation. Second, the CD45-ve cell fraction was subjected to 84-1 positive selection. Briefly, cells were labeled with 84-1 antibody and later mouse IgG binding microbeads were added to the mixture. 84-1 +ve cells were then extracted using the magnetic column from Miltenyi Biotec. The cells thus obtained are 84-1 positive and CD45 negative and are ready for further analysis.

Flow Cytometry.

Half a million cells were detached by trypsinization, washed, and stained for 20 min on ice in the dark. For CSV analysis, cells were stained with 84-1 mAb (1:100) and as an isotype control (Invitrogen) for mouse primary antibody was used. Later cells were rinsed twice in PBS and labeled for secondary antibody using AlexaFluor-405, -488, and -555 secondary antibodies (Invitrogen). Cells were then washed twice in PBS and used for data acquisition immediately using Attune Flow cytometer (Applied Biosystems). Ten to 50,000 cells were counted for the analysis. Data was later analyzed using FlowJo software (Treestar). Mean fluorescence intensity was measured using the algorithm provided by FlowJo software and was later evaluated for CSV presence on the surface. Alternatively, cells obtained after RBC lysis were subjected to dual staining using 84-1 antibody against CSV and CD45 antibody. Samples were compensated using antibody capture Abc beads (Invitrogen). Dot plots were plotted with CSV positive gating and CD45 negative gating to enumerate the CTCs in a given sample. Isotype controls were utilized to gate the unstained and non-specific stained cells. Entire cell population was analyzed for CTCs using Attune Flow Cytometer and analyzed using FlowJo software.

Microscopy Image Capture and Analysis.

A total of 5,000 cells per chamber were grown on Lab-Tek 8-well permanox chamber slides (Thermo Scientific, Rochester, N.Y., USA) as described above. For cell surface staining, cells were fixed using 4% paraformaldehyde for 15 min, washed with PBS pH 7.4, blocked in 10% fetal calf serum (FCS) (Gibco, Invitrogen) for 1 hr and labeled for respective primary antibody (1:100) overnight at 4° C. Cells were then rinsed in PBS pH 7.4 and stained using Alexafluor-488 and -555 secondary antibodies (1:250) (Invitrogen) against respective primary antibodies.

For nuclei staining, DRAQ5 (Cell Signaling) (1:500) was incorporated along with secondary antibodies for 60 min. WGA (Invitrogen) was used for staining the cell-surface, at 1:1000 for 5 minutes. The cells were then washed with PBS pH 7.4 (3×15 min) and mounted in Slowfade antifade (Invitrogen). For intracellular staining, cells were fixed as described above, washed with PBS pH 7.4, and permeabilized in PBS pH 7.4/0.2% NP40 (Sigma Aldrich) for 20 min. Blocking, primary, and secondary antibody incubations and mounting are as described above. For staining 3D culture spheres, the above extracellular and intracellular staining methods were utilized with modified time incubations of primary antibody for 36 hr and secondary antibody for 4 hrs.

For in vivo labeling of cells, total cell mixture obtained after RBC lysis was washed in PBS pH 7.4 twice and labeled using 84-1 antibody for 20 min on ice, stained cells were then washed twice in PBS pH 7.4 and stained for secondary antibody Alexafluor-488 against 84-1 for 20 min and after washing twice in PBS pH 7.4, cells were plated on culture dishes and visualized for Alexafluor-488 positive cells under Jenco Epi-Fluorescence Inverted Microscope and pictures were obtained using the supplied software. Only high intensity green fluorescent cells were considered for the analysis. The sensitivity of this assay was confirmed by cell spiking assays. For live cell imaging, laser intensities were kept to the minimum required to obtain an image to minimize photobleaching and phototoxicity. Alternatively after CD45 depletion, cells were stained for 84-1 and CD45 (AbCAM) using respective antibodies and plated on a glass slide using Cytofuge (Iris) and analyzed for 84-1+ and CD45-cells using confocal microscopy.

For confocal analysis, images were acquired in 8 bits with a Zeiss LSM 510 confocal microscope using LSM 5 3.2 image capture and analysis software (Zeiss). A 63× water-immersion objective (NA, 1.0) was utilized with digital zoom for image capture. All images were acquired by the same user using the same intensity and photodetector gain in order to allow quantitative comparisons of relative levels of immunoreactivity between different samples.

Spiking Assay.

To demonstrate the capturing precision and reproducibility by 84-1 antibody, cultured cancer cells were spiked in to blood collected from naïve mice. For precision demonstration, ~5, ~25, and ~50 of K7M3, K7, LMB, and DUNN were spiked in to 1 mL of whole blood in triplicate. For cell counting, cells were harvested in culture medium and then serially diluted to achieve the required counts, which were then confirmed in a series of 5 µL spots under a microscope. Under circumstances where in lower/higher number of cells were observed, calculations were performed to mix and obtain the necessary counts of cells required to be spiked. Spiking experiments were performed in triplicates to ensure the sensitivity and specificity of the method. For negative controls, CSV negative cells were spiked into blood and analyzed for positive selection.

Mutation Analysis.

Whole genome amplification from small numbers of CTC cells or single cells were performed using the REPLI-g Mini Kit (QIAGEN, Valencia, Calif.). Briefly, cell material in 4 µl PBS was lysed by adding 3 µl Buffer D2 in a micro centrifuge tube and incubated for 10 min at 65° C. Whole genome amplification was carried out in the same tube following the manufacturer's recommendation. Resulting DNA was tested for quality by PCR with primers on different chromosomes. Aliquot of amplified DNA was diluted 1:10 and subsequently used for PCR analysis. For gene mutation detection, Q5® High-Fidelity DNA Polymerase (NEB, Ipswich, Mass.) was used to amplify specific gene fragments for specific mutation sites. PCR products were gel purified with Qiaquick Gel Extraction Kit (Qiagen, Valencia, Calif.) and Sanger sequenced by MDA Sequencing and Microarray Facility (MD Anderson Cancer Center).

Marker Analysis.

Antibodies against specific markers were used for each type of cancer; CD99 (Abcam), α-SMA (Abcam), CD-31 (eBioscience) and EpCAM, Slug, E-Cadherin, β-catenin, c-myc (Cell signaling).

Western Blotting and Immunoprecipitation.

Recombinant human vimentin (rhVim) (R&D Systems) was loaded in three different lanes (1, 10 and 1000 ng) and were separated using SDS gels and transferred onto polyvinylidene difluoride membranes. Detection of rhVim was by incubation of the membranes using 84-1 antibody (1:1000). The secondary goat anti-mouse IgG: HRP (horse radish peroxidase) (Promega) was used to detect 84-1 antibody. For immunoprecipitation, LM7 cells were lysed using immunoprecipitation buffer (Thermo Scientific) and vimentin was immunoprecipitated using 84-1 and 12-1 antibodies. Mouse IgG was used as a control antibody. The immunoprecipitates were blotted using rabbit monoclonal anti-vimentin antibody (Cell Signaling).

Sodium Orthovanadate Treatment.

LM8 cells plated on 8-well chamber slides and WBC in suspension were subjected to sodium orthovanadate (SOV) (100 µM) or PBS as a control. After 18 hr incubation, the cells were then processed for immunofluorescence staining using the above described method for extracellular staining. For flow cytometric detection, cells in 6-well plates were treated with SOV (100 µM) or PBS as a control. After overnight incubation, cells were processed for flow cytometric analysis as described above. For human blood specimens, mono-nucleated cells obtained from the CPT tubes were treated with SOV (100 µM) or control PBS for 15 min. Cells were then subjected to immunofluorescence staining directly using the extracellular staining method.

Animal Studies.

Five six- to eight-week old C3H and Balb/c (NCI) mice were maintained as per NIH guidelines All animal protocols have been reviewed and approved by the Institutional Animal Care and Use Committee at the University of Texas MD Anderson Cancer Center. Mice were housed according to the institutional requirements. LM8 and CT-26 cancer cell lines were used for the in vivo inoculation and were maintained in DMEM/F-12 with 10% FBS and 0.1% penicillin/streptomycin. Confluent CT-26 and LM8 cells were dissociated from the culture plates and $1\times10^5$ cells were suspended in 15 µL PBS for intraosseous (i.o.) inoculations. Intraosseous inoculations were performed by inserting a 27 gauge, ½-inch needle insulin syringe (BD Bioscience) directly into the right tibia, and then suppressing the plunger on the syringe. Tumor volume was measured every week with blood collection as mentioned above. The sub-mandibular bleeding method was used to repetitively collect blood from the mice, which is minimally invasive. Utilizing this method, 200 µL blood samples were collected for analysis of CTC. No normal epithelial or mesenchymal cells were detectable in any of these blood samples irrespective of the presence of tumor. After optimizing the assay and route of blood collection, the CTCs in mice implanted with tumors of LM8 and CT-26 cells were enumerated.

Figure 4A:
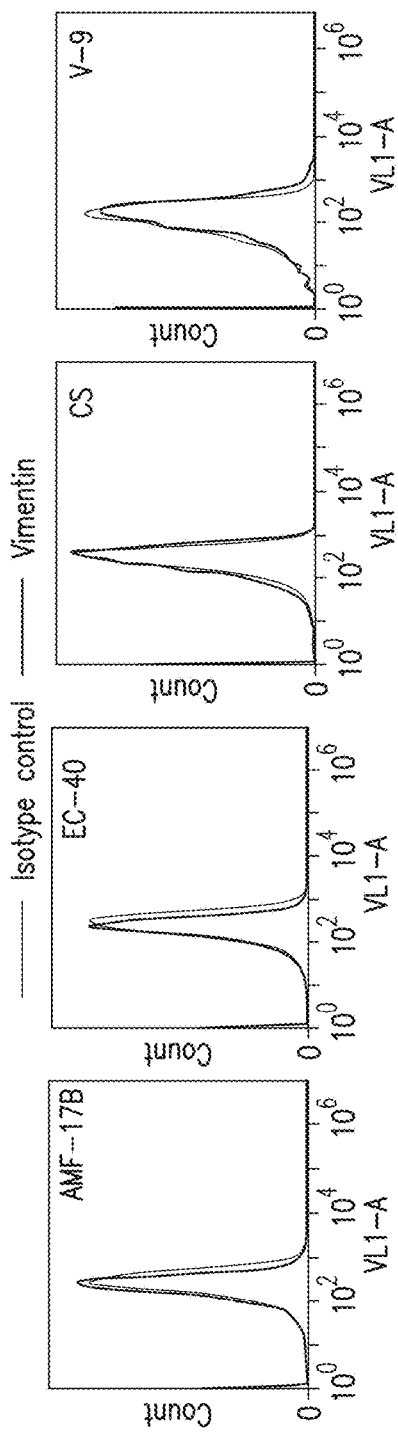
FIG. 4A: Immunological assessment of CSV in osteosarcoma cell line LM7 using commercially available antibodies. AMF-17B, EC-40, CS and V-9 antibodies were utilized for the detection of CSV on LM7 cells using flow cytometry, however there was no binding observed using these antibodies.
Figure 4B:
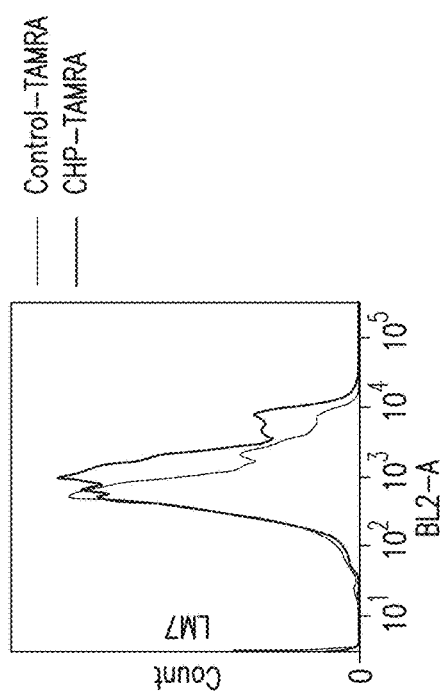
FIG. 4B: Immunological assessment of CHP-TAMRA peptide to LM7 osteosarcoma cell line using flow cytometry. CHP-TAMRA peptide binds to LM7 cells, indicating the presence of CSV on these cells.
Figure 4C:
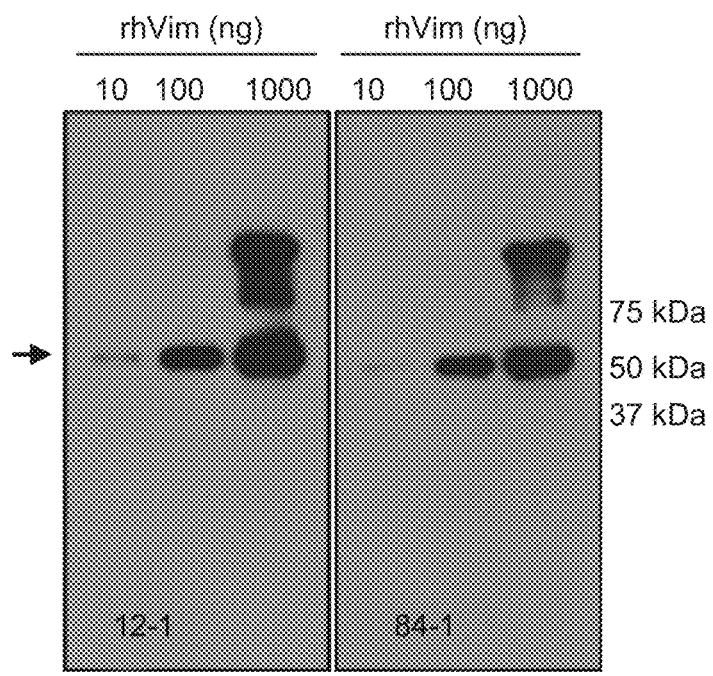
FIG. 4C: Evaluation of 84-1 and 12-1 binding to rhVim protein using western blotting. 10, 100 and 1000 ng of rhVim was loaded on 4-20% gradient gels and the western blotting was performed. Blots were probed with 84-1 and 12-1 antibody. It was observed that the antibodies have very high affinity for total vimentin.
Figure 4D:
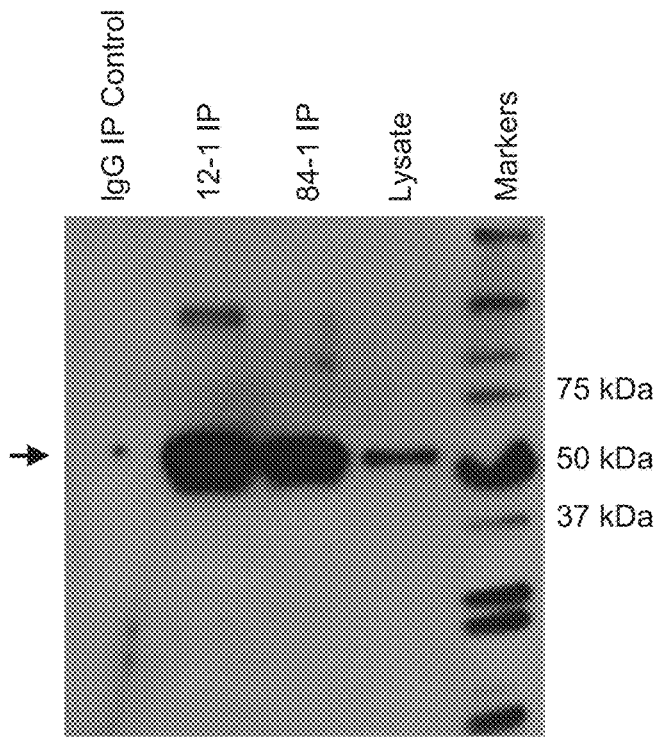
FIG. 4D: Cell lysates from LM7 cells were prepared and immunoprecipitation was performed using 84-1 and 12-1 antibodies and western blotting was performed. Blot was probed with cell signaling antibody (rabbit origin, to exclude IgG bands).
Figure 4E:
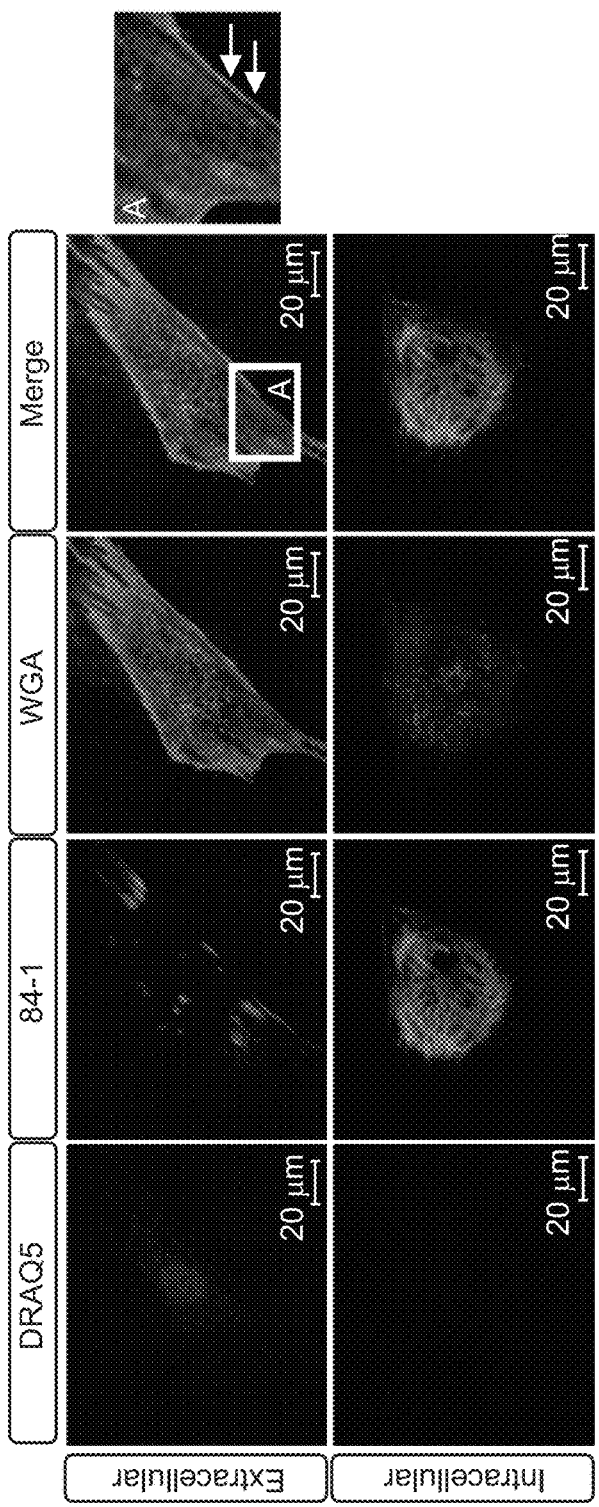
FIG. 4E: Intracellular and extracellular vimentin staining analysis in cancer cell line using confocal microscopy: HLM-3 (liver cancer) cells were stained for CSV, WGA and nuclear stain DRAQ5. 84-1 binding in non-permeabilized cells was exclusively specific to membrane, while permeabilized cells showed total vimentin levels. Scales indicate 20 µm.

Example 2—Cell-Surface Vimentin, a Novel Universal Circulating Tumor Cell Marker Vimentin over expression is frequently associated with EMT (reviewed in Satelli and Li, 2011), a process wherein the cells gain increasing invasion and metastatic potential via transition from epithelial to mesenchymal phenotypes. Single cell profiling of CTC isolated from cancer patients indicates the overexpression of vimentin transcript when compared to established cell lines (Powell et al., 2012) indicating a possibility of EMT phenotype in these CTC; however, intracellular expression of vimentin in normal mesenchymal cells, including most of the white blood cells (WBC), limits its usage as a CTC marker. Several groups, including the inventor's, have previously reported the detection of vimentin on the surface of cancer cells (Satelli and Li, 2011; Cutrera et al., 2011; Huet et al., 2006). Unlike intracellular vimentin, cell-surface vimentin (CSV) expression is mainly associated with cancer cells and was found in both epithelial and mesenchymal cancers. The inventors therefore hypothesized that CSV serves as a potential marker for CTC. However, due to the limitations of CSV binding peptide and unavailability of commercial antibodies that specifically bind to CSV (FIG. 4A), the inventors aimed to generate a CSV specific monoclonal antibody. In light of this, the inventors designed a strategy to isolate CSV specific antibody that binds only to cancer cells while excluding normal cells (FIG. 1A). Briefly, a large number of hybridoma clones were generated against full length human vimentin (NCBI: NP_003371.2) and antibodies screened for CSV binding utilizing flow cytometry by targeting CSV on an osteosarcoma (LM7) cell line, which showed positive binding for CSV specific peptide (FIG. 4B). For negative binding, normal cell lines HFOB and NCM-356 were utilized. Utilizing this strategy, the inventors identified a monoclonal antibody (Table 7), or a cell-surface vimentin binding fragment thereof, from hybridoma 84-1 which bound specifically to vimentin. The specificity of 84-1 towards vimentin was further confirmed using western blotting, immunoprecipitation and immunofluorescence (FIGS. 4C, D, and E).

Figure 5A:
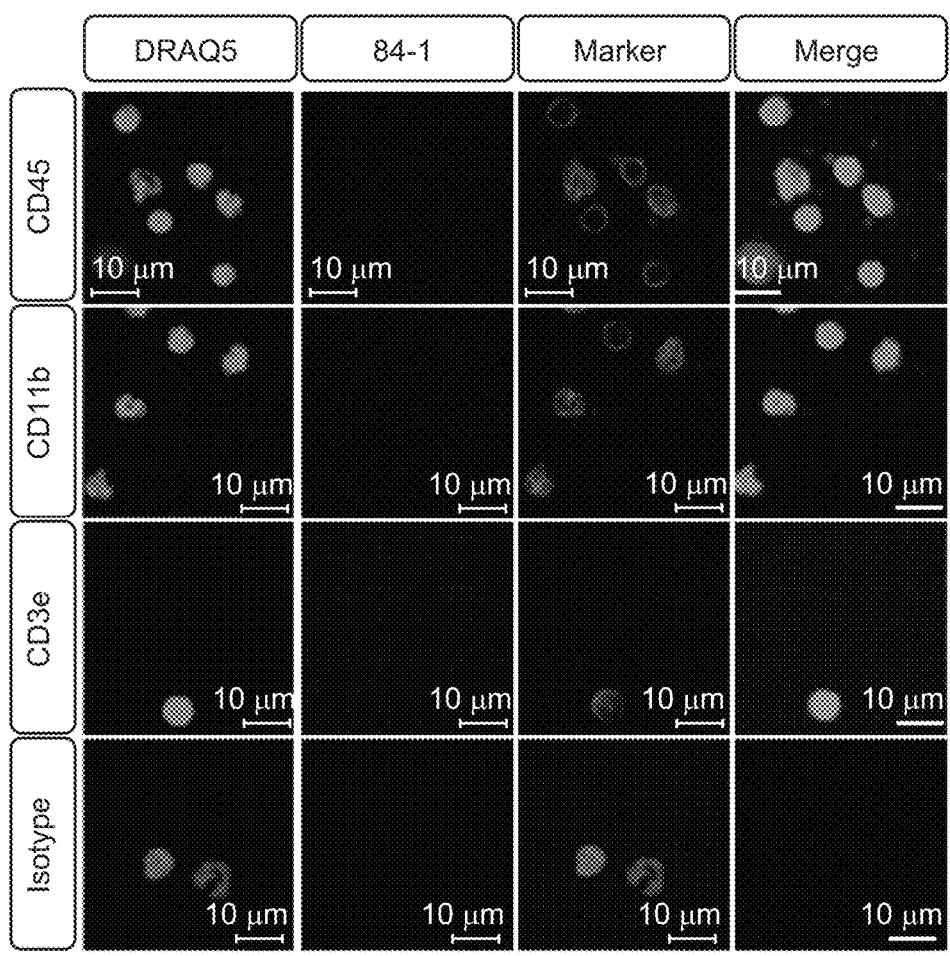
FIG. 5A: Evaluation of PBMC population from human blood for CSV staining using immunofluorescence imaging. PBMC population was isolated from human blood and evaluated for different markers including CD3e, CD11b, and CD45 staining along with 84-1. These cells did not show any strong immunostaining with 84-1 antibody. Scale indicates 10 µm.

Cell-surface screening of different epithelial, non-epithelial cancer, and normal cell lines indicated the presence of vimentin only on the surface of cancer cells (FIGS. 1A and B). Importantly, although macrophages, endothelial cells, neutrophils, platelets, and apoptotic T lymphocytes have previously been reported to express CSV (Moisan and Girard, 2006; Bhattacharya et al., 2009; Mor-Vaknin et al., 2003), this expression was nearly undetectable by 84-1 (FIG. 5A), indicating the specificity of 84-1 toward cancer CSV.

Figure 1D:
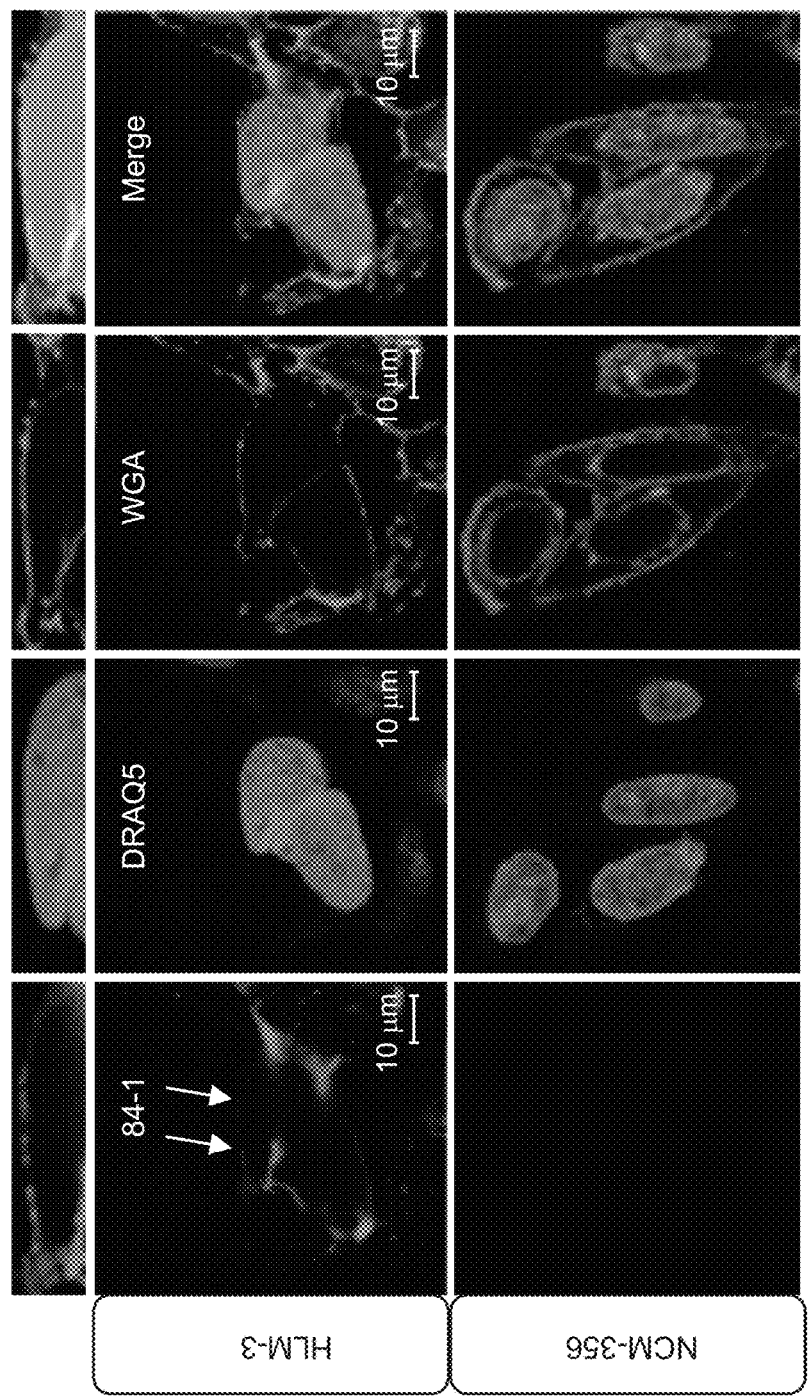
FIG. 1D: Cell surface staining analysis for CSV in normal and cancer cell line using confocal microscopy: HLM-3 (liver cancer) and NCM-356 (normal colon) cells were stained for CSV, WGA (cell-surface marker) and nuclear stain DRAQ5. 84-1 binding indicates cell surface vimentin that co-localizes with WGA, as evidenced from the magnified part of the figure that is indicated with white arrows. Scales indicate 10 µm.
Figure 1E:
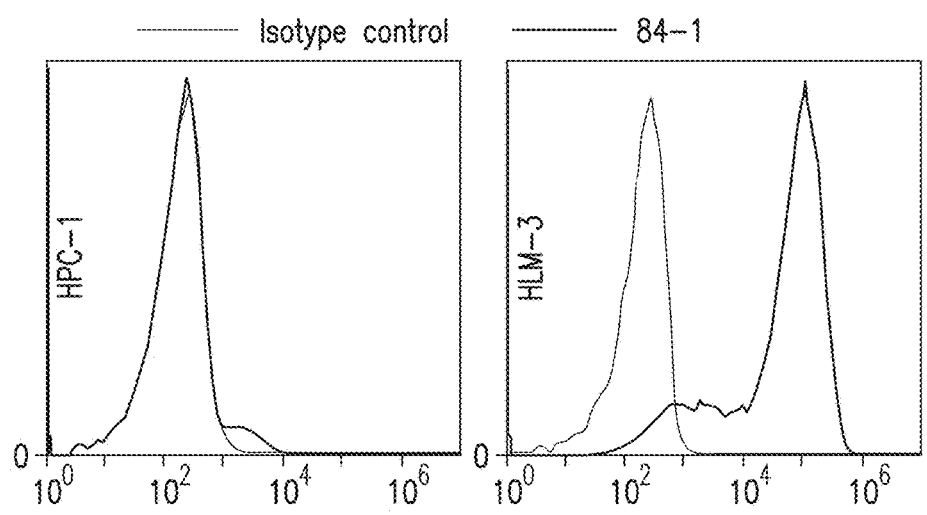
FIG. 1E: Immunological assessment of CSV in human primary and metastatic cancer cells using flow cytometry: analysis of human primary colon cancer (HPC1) and human liver metastatic cancer (HLM3) indicated the abundant expression of CSV on HLM3 compared to primary HPC1 cells.
Figure 1F:
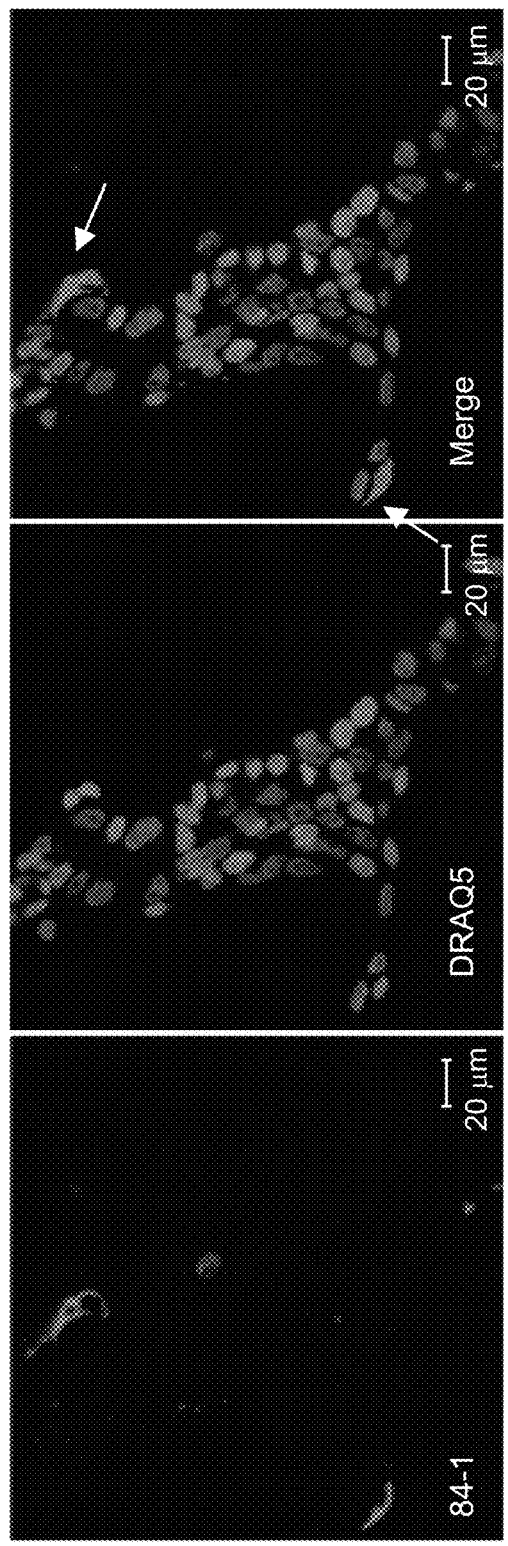
FIG. 1F: CSV detection in HPC1 derived spheres on thin Geltrex coated wells using confocal microscopy: CSV was detectable in few cells at the periphery of the sphere. Nuclear stain DRAQ5 was used to demarcate the cells. Scale indicates 20 µm.
Figure 5B:
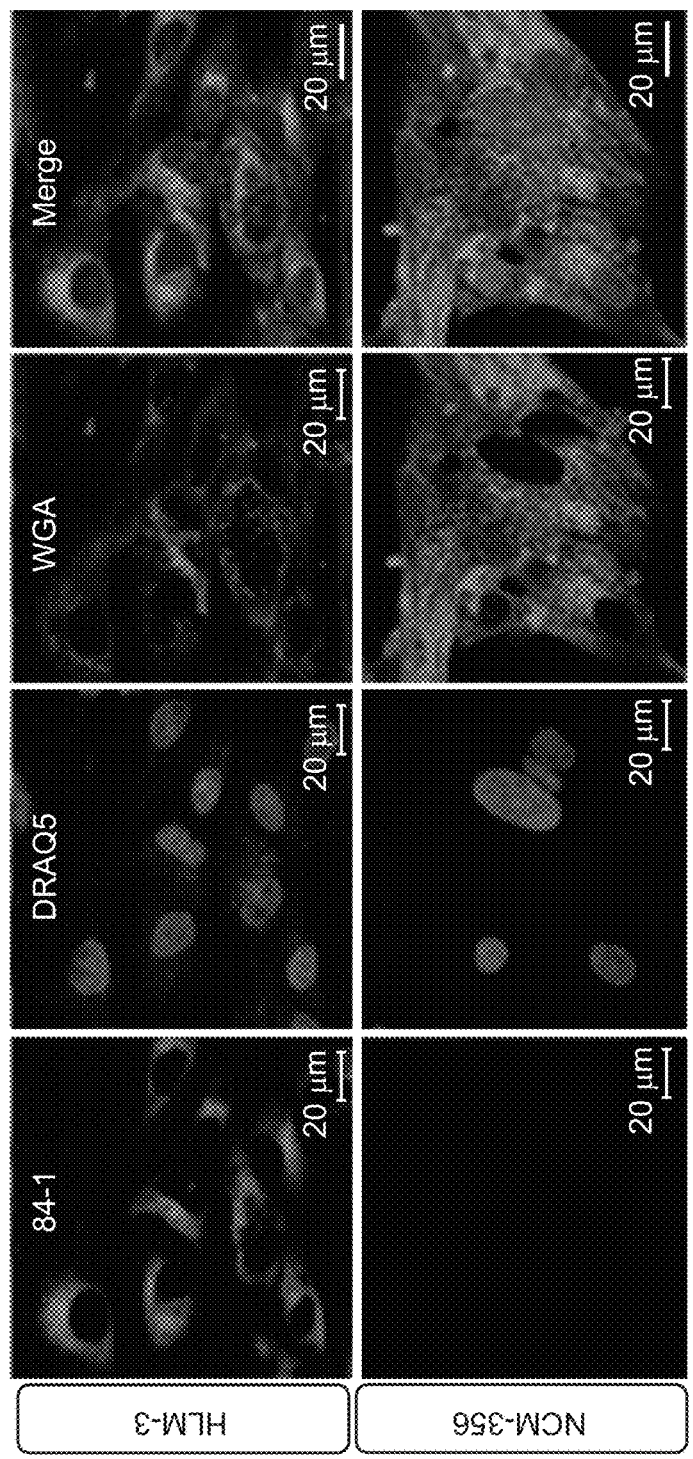
FIG. 5B: Intracellular vimentin staining analysis normal and cancer cell line using confocal microscopy: HLM-3 (liver cancer) and NCM-356 (normal colon) cells were stained for CSV, WGA (cell-surface marker) and nuclear stain DRAQ5. 84-1 binding indicates presence of vimentin only in HLM3 cells in comparison to NCM-356 cells. Scales indicate 10 µm.
Figure 5C:
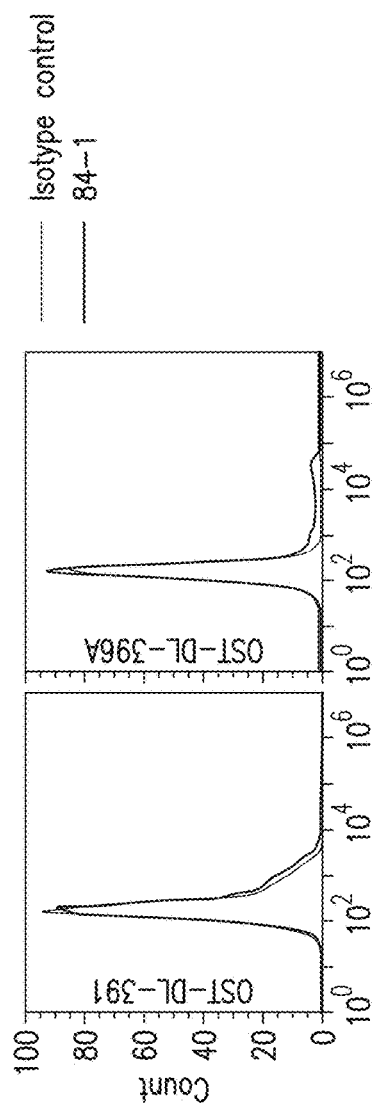
FIG. 5C: Immunological assessment of CSV in cells isolated from osteosarcoma patient samples using flow cytometry: analysis of OST-DL-391 (no metastasis) and OST-DL-396A (metastasis to brain) indicated increased fraction of cells with CSV on OST-DL- 396A compared to that of OST-DL-391 cells.
Figure 5D:
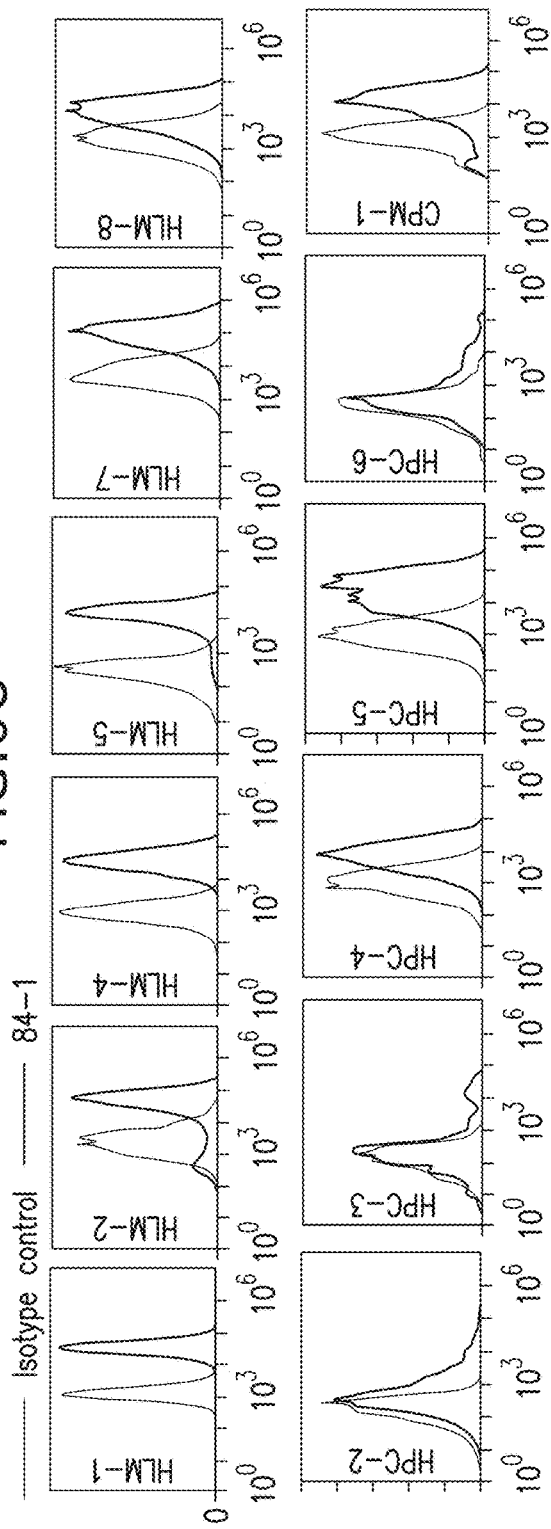
FIG. 5D: Immunological assessment of CSV in human primary and metastatic cancer cells using flow cytometry: analysis of human primary colon cancer (HPCs) and human liver metastatic cancer (HLMs) indicated the abundant expression of CSV on HLM3 compared to primary HPC1 cells. CPM-1 represents cells isolated from lung cancer that metastasized from colon and showed increasing CSV in comparison to that of primary cancer cells.
Figure 5E:
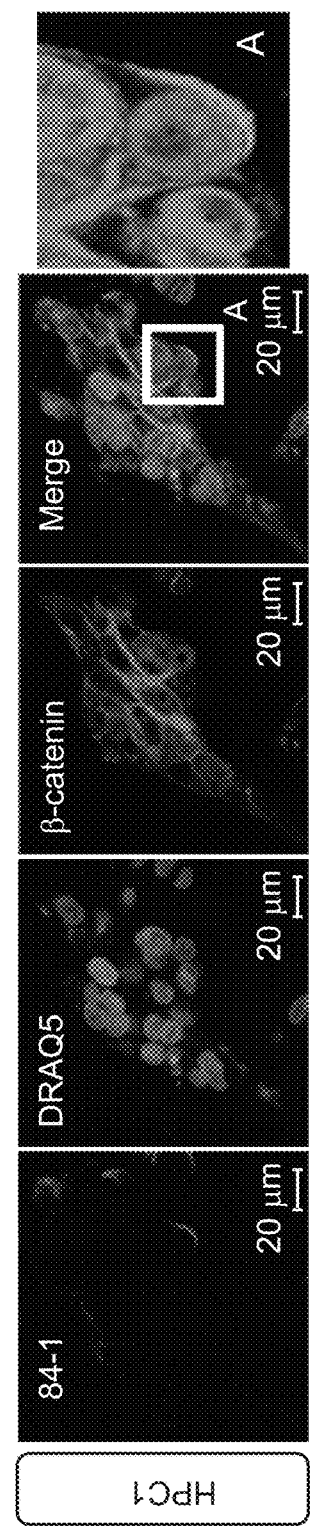
FIG. 5E: Vimentin and β-catenin expression in HPC1 derived spheres on thin Geltrex coated wells using confocal microscopy: Total vimentin was detectable in few cells at the periphery of the sphere that correlated with increased nuclear accumulation of β-catenin. Nuclear stain DRAQ5 was used to demarcate the cells. Scale indicates 20 µm.

The inventors have tested a range of cancer cell lines that originate from breast, bladder, brain, colon, liver, lungs, pancreas, skin tissues, and blood, which show a distinct population of cells with CSV expression (Table 1) Immunocytochemistry analysis of human liver metastatic cells (HLM-3) indicates the presence of vimentin on the surface of the cells (FIG. 1D) that co-localizes with cell-surface marker Wheat Germ Agglutinin (WGA) and is undetectable in normal colon epithelial cells (NCM-356). Permeabilizing these cells indicated the presence of cytoplasmic vimentin only in HLM-3 cells, while NCM-356 cells were negative (FIG. 5B). An analysis of the primary cancer cell lines generated from human osteosarcoma patient samples (FIG. 5C) shows expression of CSV in metastatic cell lines while primary cell lines were negative (Table 2). Further analysis of cancer cells isolated from human colon and metastatic liver (from colon) tissues for CSV showed very high expression in liver metastatic samples compared to primary colon cancer samples (FIGS. 1E and 5D), suggesting that CSV could serve as a potential biomarker for the metastatic cancer cells. Although, primary colon cancer cells showed subtype of cells with lower expression of CSV, it is possible that these cells are of invasive/metastatic phenotypes that are shed into the blood circulation for spreading to distant organs. This hypothesis is supported by the presence of CSV positive cells at the periphery of the sphere in a 3D sphere model (FIG. 1F), suggesting the possibility that these cells are of more aggressive and invasive phenotypes, which is supported by the increasing nuclear accumulation of β-catenin that represents the invasive phenotype of these cells (Brabletz et al., 2005) (FIG. 5E).

Figure 2A:
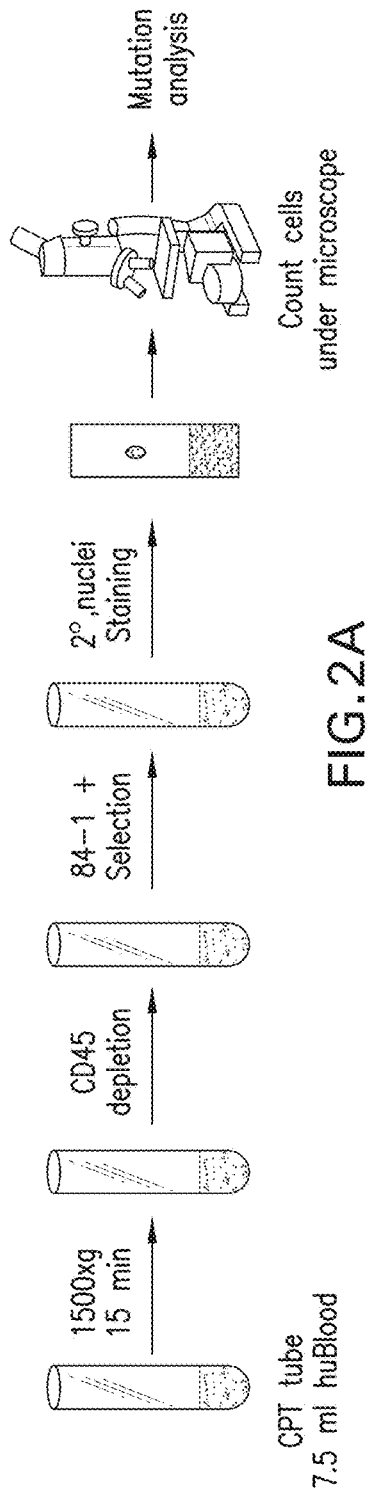
FIG. 2A: Schematic representation of 84-1 mediated CTC detection, isolation, enumeration and analysis.
Figure 2E:
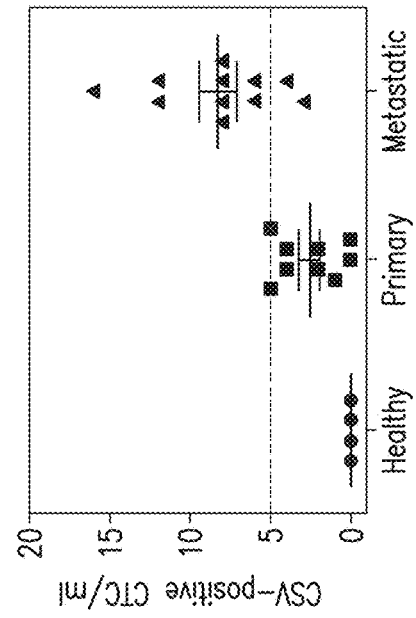
FIG. 2E: Enumeration of CSV positive CTCs from healthy, primary and metastatic patient blood specimens. Blood from the primary cancer patients was used to select threshold of detection (dashed line). Metastatic cancer patient samples showed higher CTC counts comparatively.
Figure 2B:
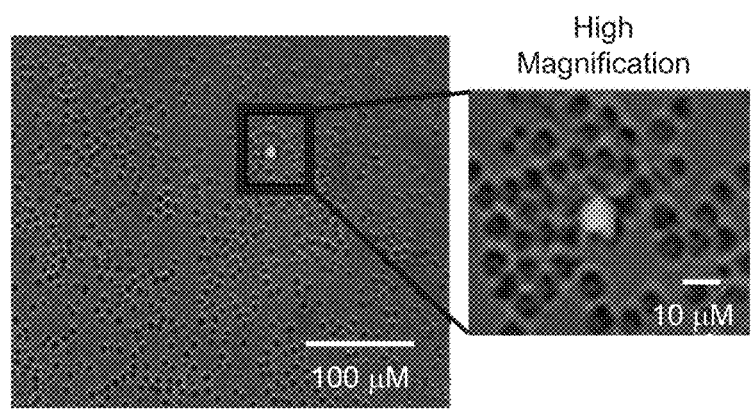
FIG. 2B: Detection of single cell spiked into blood using fluorescence microscopy. Single LM8 cell was isolated using serial dilution and spot analysis and spiked into 1 ml of blood. After RBC lysis, mononucleated cell population was stained for 84-1 mAb and AlexaFluor-488 secondary antibody to detect CSV positive cells. High magnification shows the detection of single cell in whole blood population that is CSV positive.
Figure 2C:
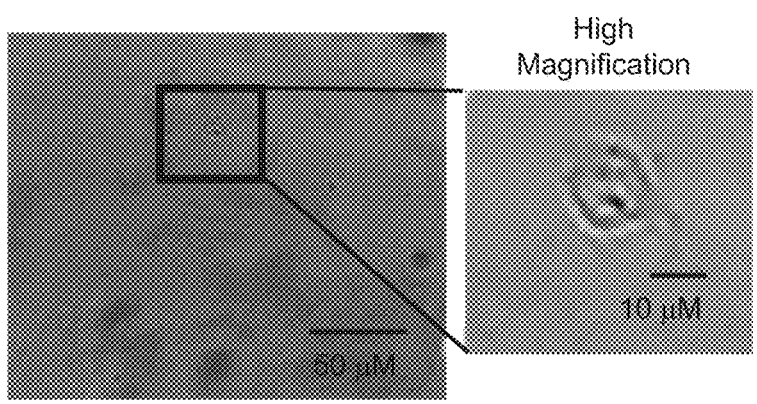
FIG. 2C: Isolation of single cell from whole blood. Single cell spiked into whole blood was isolated using EasySep based 84-1 positive and CD45 negative selection. This single cell was observable on the culture dish 2 hr after incubation at 37° C.
Figure 2D:
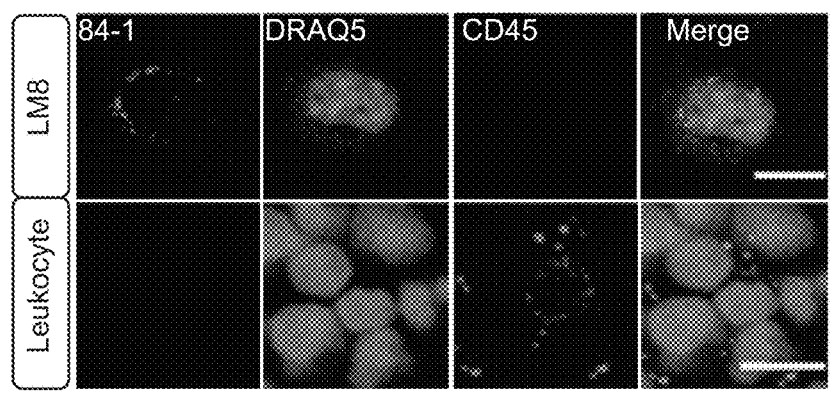
FIG. 2D: Micrographs of cells isolated from blood were costained using antibodies against CSV, CD45 and a nuclear stain DRAQ5. Scale indicates 10 µm.
Figure 6A:
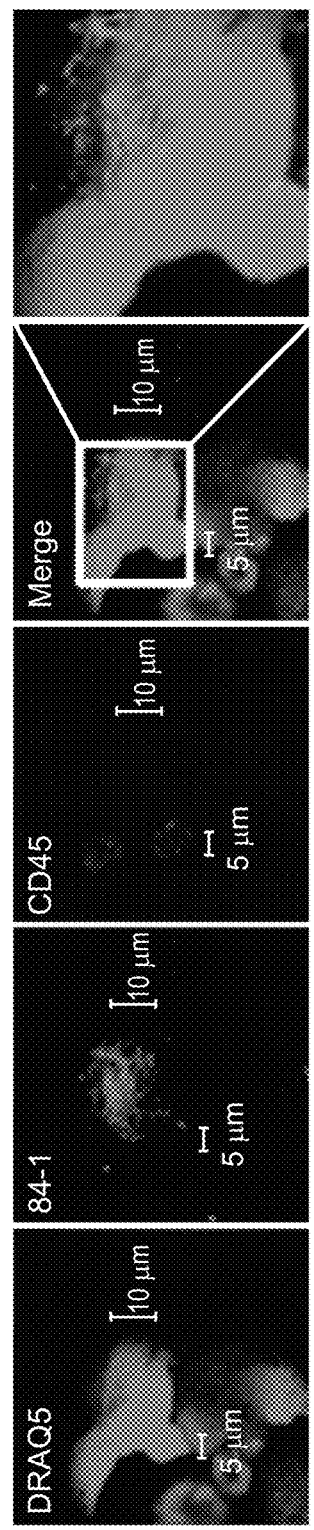
FIG. 6A: Interaction between tumor cells and immune cells. Mononucleated population isolated from the blood was evaluated for 84-1, CD45 and DRAQ5 staining Immune cells that were CD45 positive were interacting with 84-1 positive tumor cells as determined by the size of the nucleus.
Figure 8:
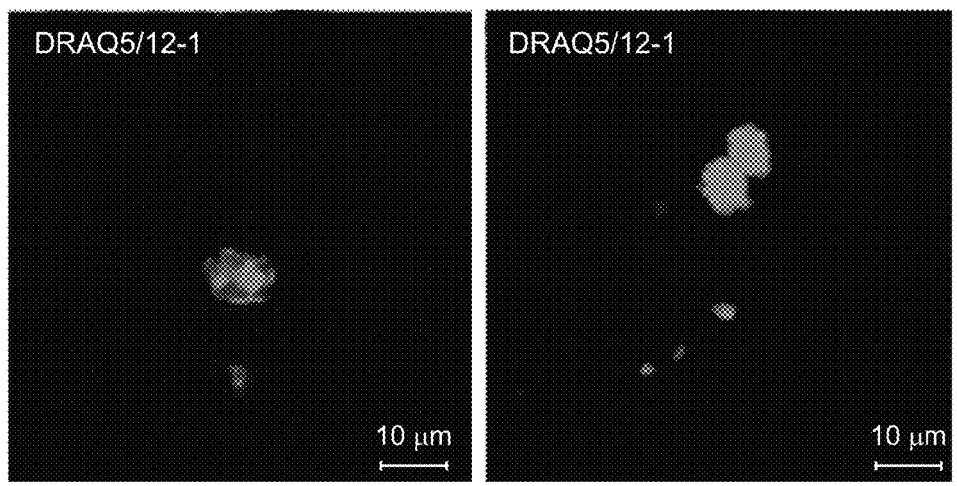
FIG. 8: LM7 cells extracted using 12-1 monoclonal antibody were stained for cell surface vimentin using 12-1 antibody and DRAQ5 (nuclear stain). Scale bar indicates 10 µm.

Based on the detection of CSV in a range of cancer cell lines of both epithelial and non-epithelial origin, the inventors hypothesized that it could serve as a biomarker to detect CTC. To test this hypothesis, the inventors tested the detection of well characterized mouse metastatic LM8 cells, which were spiked into 7.5 mL of blood and subjected to immunofluorescence staining using 84-1 antibody (schematic representation in FIG. 2A). From micrographs it is evident that single cell is detectable in whole blood utilizing fluorescence microscopy (FIG. 2B). Utilizing magnetic separation with 84-1 conjugated beads, the inventors were also able to isolate the single cell from whole blood (FIG. 2C) and visualize it in a culture dish, suggesting the isolation of viable cells. Further, the isolated cells were characterized further using confocal imaging and confirmed as cancer cells based on the size of the nucleus (>8 μm) and positive staining for CSV and negative staining for CD45, a leukocyte marker (FIG. 2D). In rare instances, the inventors did observe interactions between tumor cells and immune cells (FIG. 6A). The inventors further evaluated the sensitivity and specificity of 84-1 antibody using HLM3 and LM7 cells that are positive for 84-1 staining (Table 5). The results indicated a very high sensitivity and ~100% specificity of the antibody in detecting CTC. Additional spiking assays were performed using another isolated cell surface vimentin-binding antibody, 12-1 (Table 6). The results indicated very high specificity and about 40% sensitivity of the antibody in detecting CTC. Furthermore, the LM7 cells extract using 12-1 antibody were stained for cell surface vimentin using 12-1 antibody and DRAQ5 (nuclear stain) (FIG. 8).

Figure 6D:
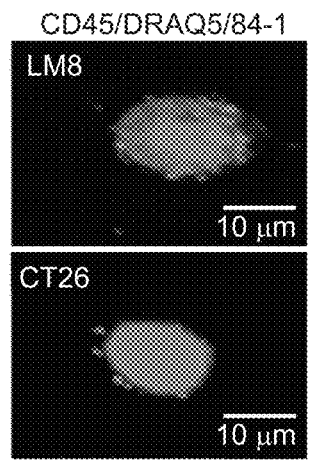
FIG. 6D: Micrographs of cells isolated from blood were costained using antibodies against CSV, CD45 and a nuclear stain DRAQ5. Scale indicates 10 µm.
Figure 6E:
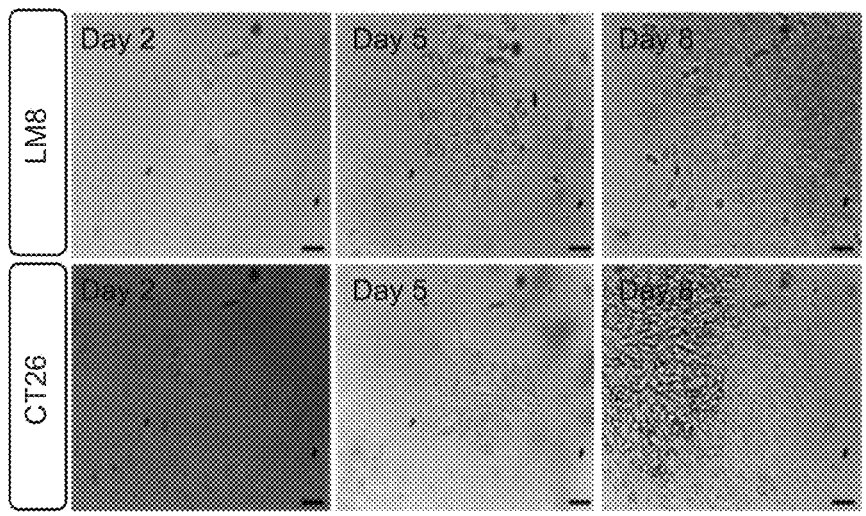
FIG. 6E: Isolation and culture of CTCs isolated from LM8 (upper panel) and CT-26 (lower panel) that were monitored for eight days for formation of cell colonies. Scale indicates 10 µm.
Figure 6F:
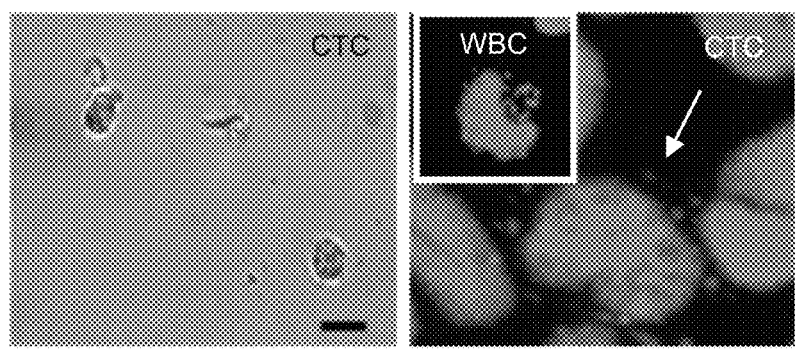
FIG. 6F: Detection of 84-1 positive CTCs in canine model. CTC from blood samples were isolated and analyzed by bright field and fluorescence microscopy. CTCs were isolated and cultured on 96 well plates and bright field images were acquired. For fluorescence imaging, CTCs were stained for CSV, CD45 and a nuclear stain DRAQ5 and analyzed by confocal microscopy. Cell viability was tested using Calcein-AM staining Scale represents 10 µm.

The spiking assays performed using 84-1 were further corroborated by in vivo studies wherein the inventors utilized the LM8 osteosarcoma cells for non-epithelial model and CT26 colon carcinoma cells for epithelial model. These mice were monitored for changes in CTCs over a period of time (FIGS. 6B and C) and at the end of the study, the cells were isolated and cultured in a culture dish (FIG. 6D) and confirmed for CSV+, CD45– and large nucleus (FIG. 6E). The inventors also utilized the spontaneous tumor model of p53 mutated mice that showed the presence of CTCs in different types of tumors that developed spontaneously over a period of time (Table 4). Furthermore, the inventors tested for CTC in the blood of canine with spontaneous tumors and interestingly 84-1 was able to detect CTCs in this model, which were confirmed by CD45 negativity and CSV positivity and based on the size of the nucleus (FIG. 6F).

Figure 3A:
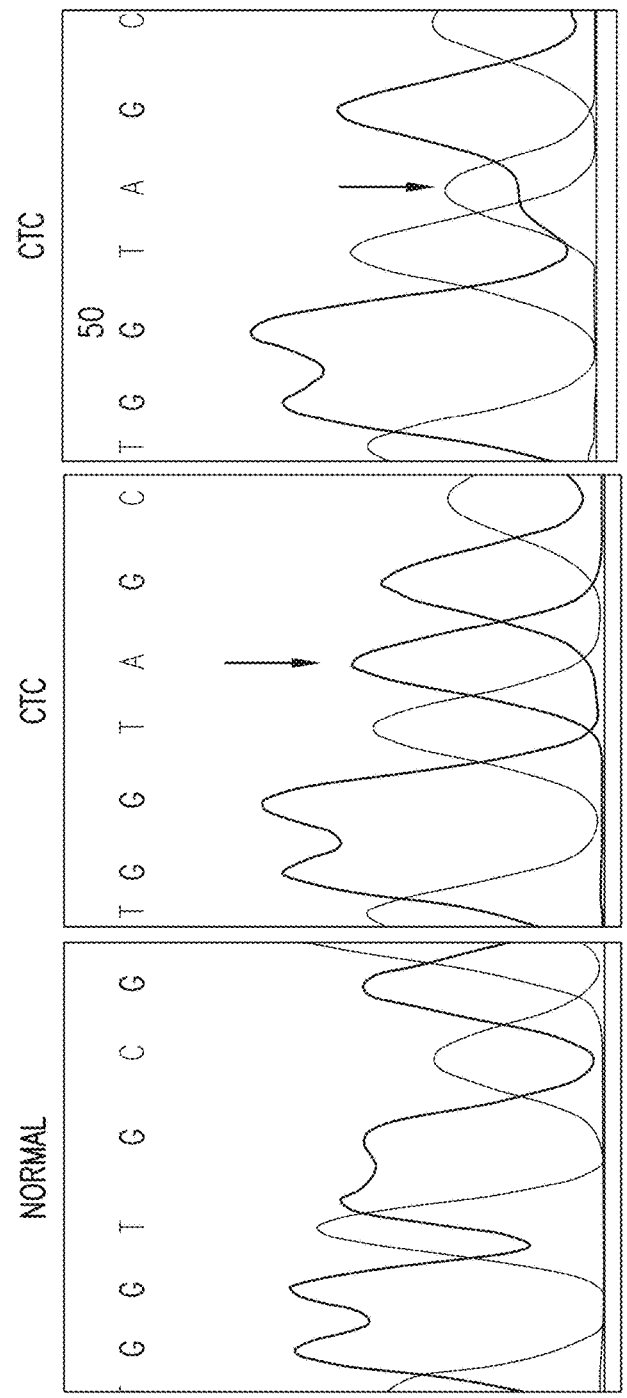
FIG. 3A: Mutational analysis of KRAS in CTC and matched leukocyte. CTC harbored homogenous (middle panel) and heterogeneous codon 13 mutation (right panel), while leukocyte had wild type sequence (left panel).
Figure 3B:
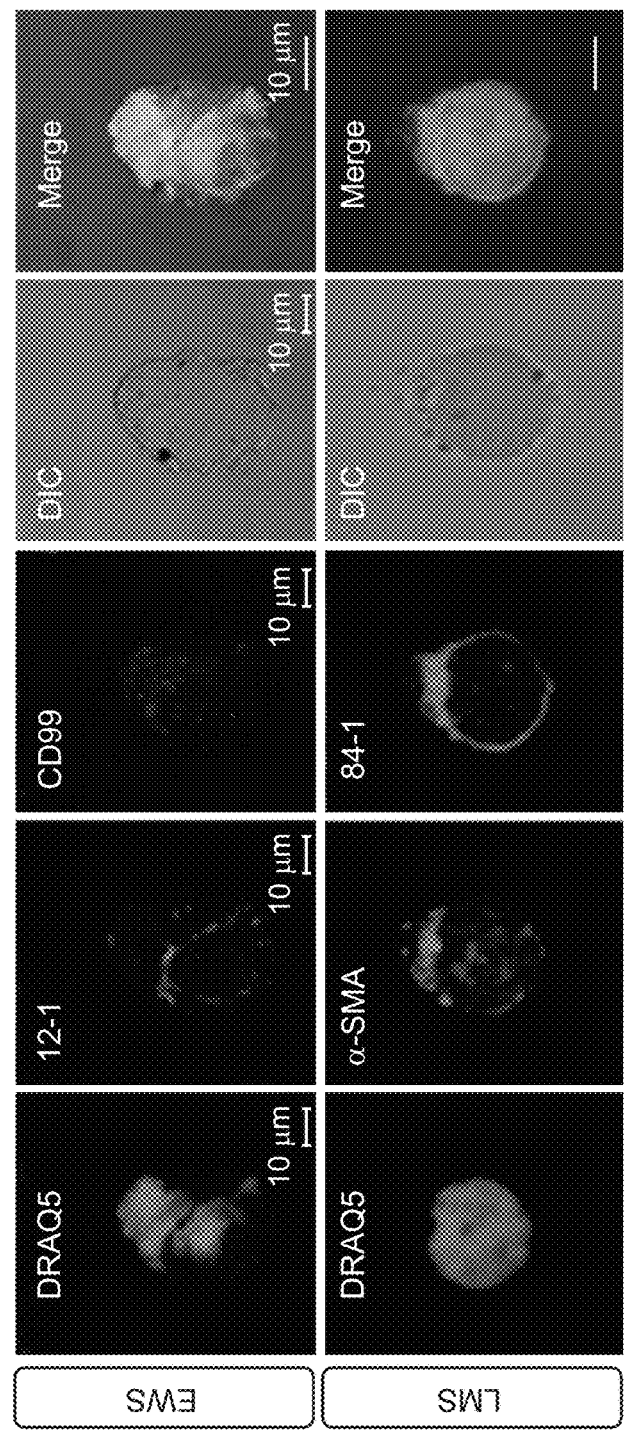
FIG. 3B: Analysis of CTCs from Ewing Sarcoma (EWS) and Leiomyosarcoma samples (LMS) samples. EWS CTC were validated using CD99 marker and LMS CTC were validated using α-SMA staining. Scale indicates 10 µm.
Figure 7A:
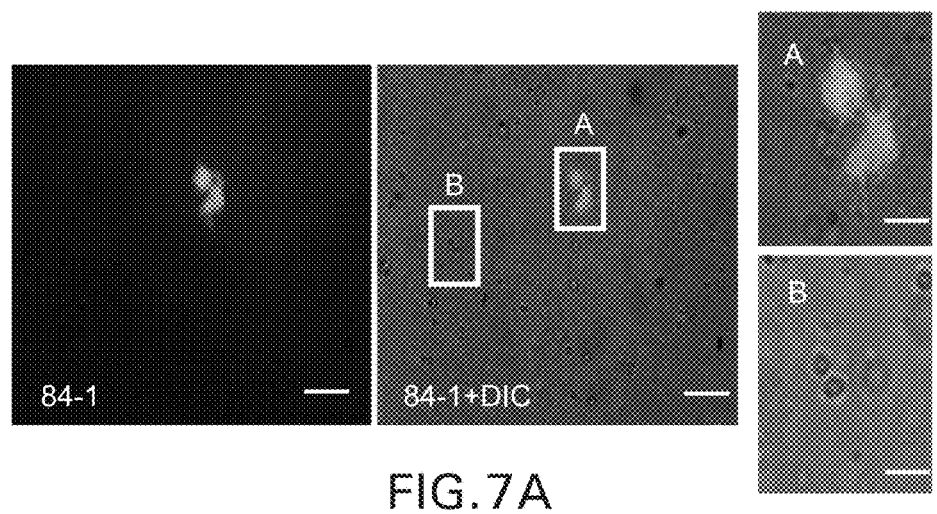
FIG. 7A: Mononucleated cells isolated from the blood of patient were stained for 84-1. It can be observed that these cells were distinct from the PBMC population in the blood.
Figure 7B:
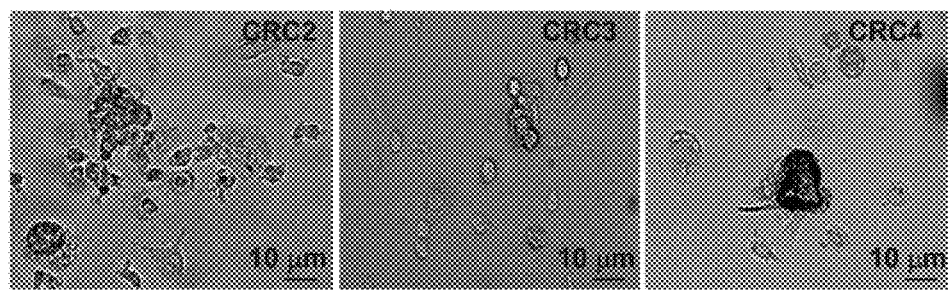
FIG. 7B: Cell culture of CTC isolated from CRC patients. 84-1+ CTC isolated from the blood of colon cancer patients were cultured in vitro in 96 well plates and were utilized for single cell analysis.

Since 84-1 antibody detected spiked cells and CTC in blood with high specificity, the inventors tested human blood samples from healthy volunteers, non-epithelial cancers including osteosarcoma, leiomyosarcoma, unidentified pleomorphic sarcoma (UPS) and epithelial cancers that include colon cancer and liver cancer for CTCs using fluorescence imaging (Table 3) and were successful in identification of CTC. No CTC were detectable in healthy blood samples. Collectively, an increase in CTC count was observed in metastatic cancer patient samples compared to primary cancer samples indicating the possible detection of highly metastatic CTC (FIG. 2E). The CTC from colon cancer patients were also visualized under fluorescence microscope before magnetic separation of 84-1+CD45– cells (FIG. 7A). 84-1+ CD45-cells isolated using magnetic beads were viable for few weeks thus enabling us to analyze these further using FISH and mutational analysis thereby confirming their identity as cancer cells (FIG. 7B). Single cells were characterized for tumor phenotype by mutational analysis. For this analysis CTCs isolated from colon cancer patient samples were used. Mutation analysis for KRAS (v-Ki-ras2 Kirsten rat sarcoma viral oncogene homolog) in CTCs indicated that the CTC harbored KRAS mutations on the codon 13 specifically, while CD45+cells isolated were used as control harbored wild type KRAS gene (FIG. 3A). It is interesting to note that although the primary tumors harbored KRAS mutation on codon 12, CTCs were tested positive for mutations on codon 13. Previous studies have reported heterogeneity in the detection of KRAS mutations in CTC isolated from the same patient (Gasch et al., 2012). Furthermore, a clinical characterization of patients with metastatic colorectal cancer depending on the KRAS status indicated that codon 13-mutated metastatic colorectal cancer represented a more aggressive and invasive disease that is frequently associated with local and distant metastasis at the time of first representation of the clinical disease (Modest et al., 2011). Also, an analysis of the KRAS mutations in bone marrow metastases and the primary tumor in colorectal cancer indicated codon 13 mutations in disseminated cells compared to codon 12 mutations in primary tumor, thereby highlighting the heterogeneous nature of the CTC (Tortola et al., 2001). These results thus indicate a potential mutation hotspot marker for CTC with aggressive phenotype and metastatic potential in colorectal cancers. For mesenchymal tumor CTC, then 84-1+ CTC isolated from blood were validated by utilizing specific markers for a given tumor; CD99 was used as a marker for Ewing sarcoma CTC and α-SMA for leiomyosarcoma (FIG. 3B). Future trials with a large set of population are warranted to draw any correlations between CSV positive CTC and the clinical outcome.

Figure 3C:
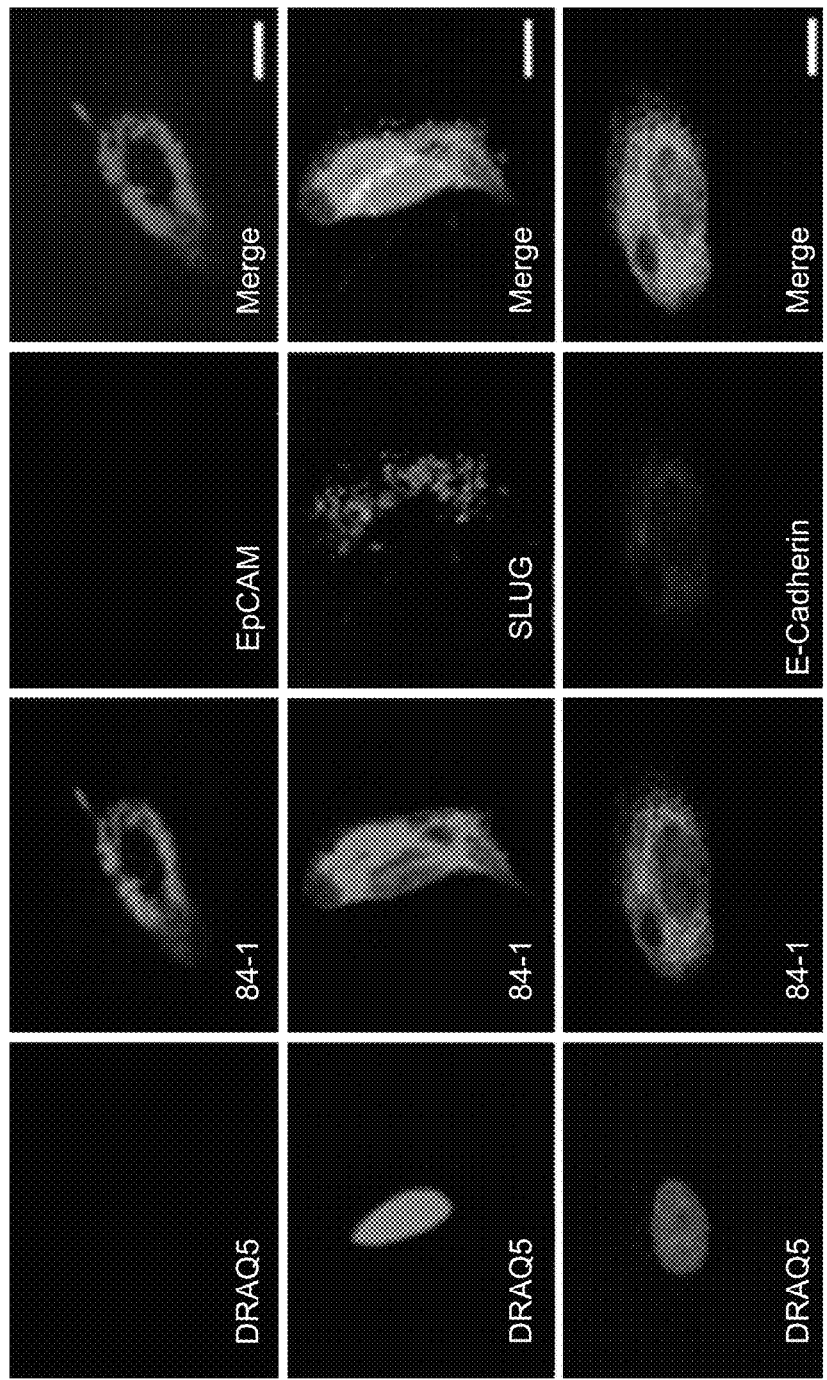
FIG. 3C: Analysis of CTCs for molecular specific markers. CTCs isolated using 84-1 mAb were stained for EpCAM an epithelial marker, SLUG an EMT specific regulator, and E-Cadherin. Scale indicates 10 µm.
Figure 3D:
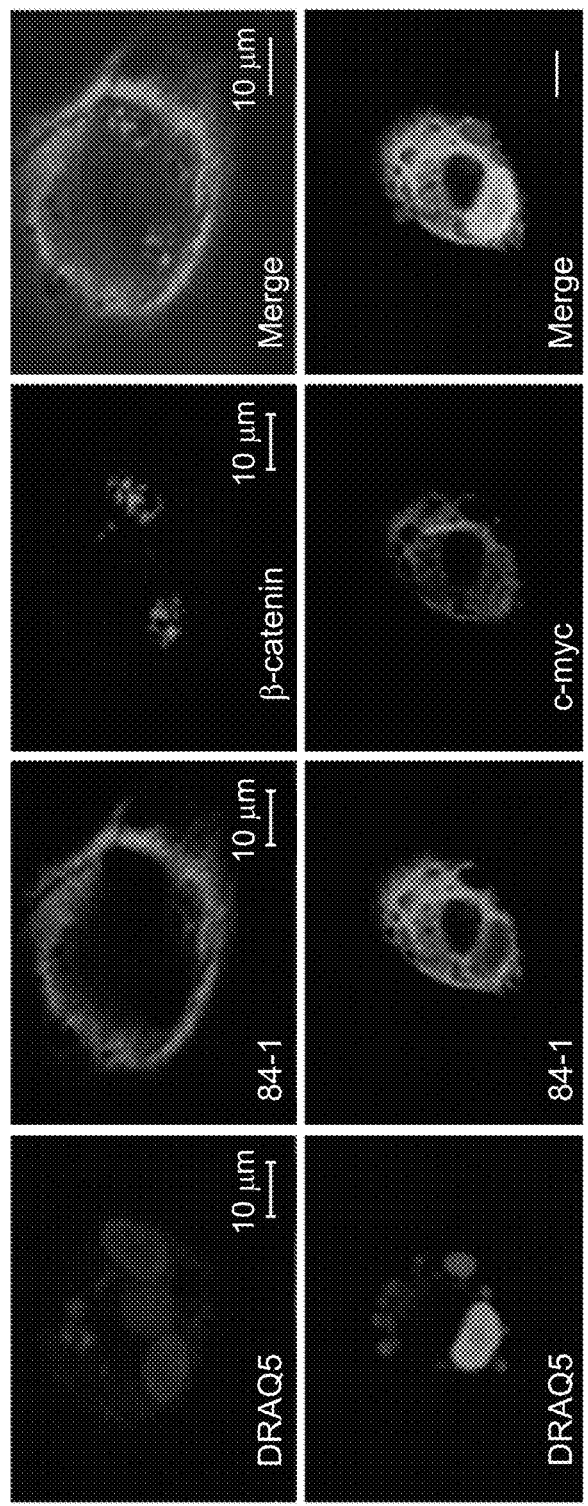
FIG. 3D: Analysis of CTCs for vimentin, β-catenin and c-myc expression. CTCs from human colon cancer samples were isolated and stained for total-vimentin, β-catenin, c-myc and nuclear stain DRAQ5, which indicated complete nuclear localization of β-catenin and c-myc in the patient samples. Scale indicates 10 µm.
Figure 7C:
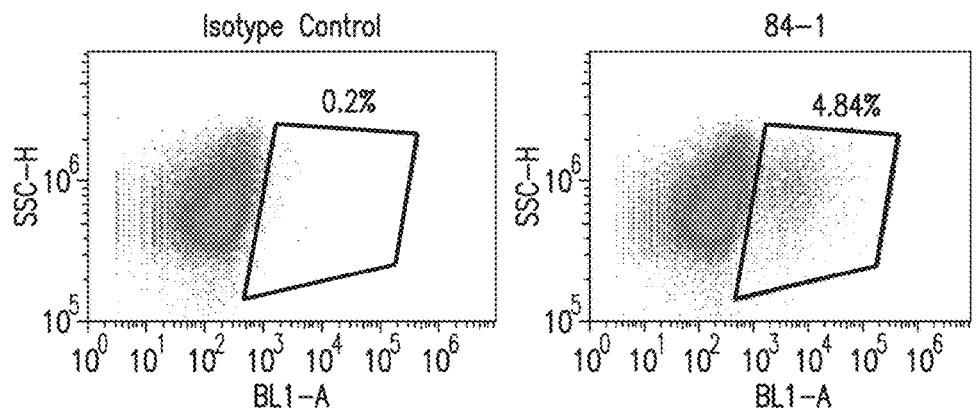
FIG. 7C: MDA-MB-468 analysis for 84-1 binding by flow cytometric analysis. MDA-MB-468 cells were stained for 84-1 and analyzed for positive fraction of cells binding to CSV.

Sieuwarts et al. (2009) have previously reported that MDA-MB-231 and MDA-MB-468 cells are normal breast like cancer cells and are characterized with invasive phenotype, but were shown to escape EpCAM mediated detection. Interestingly, these cells were detectable using the inventor's antibody utilizing flow cytometry (FIG. 7C), suggesting the detection of EpCAM negative CTCs that have possibly undergone EMT. Since our antibody was able to detect CTC from colon cancer patient samples, the inventors wanted to test if these cells have undergone EMT and are thus readily detectable due to increasing CSV expression. The 84-1+ CD45– CTC isolated were tested for EpCAM, E-Cadherin, vimentin and Slug immunofluorescence labeling using confocal microscopy (FIG. 3C). The results indicated that these CTC have lost the expression of EpCAM, a marker for epithelial phenotype of cancer cells. However, further characterization for internal vimentin confirmed their transition from epithelial to mesenchymal phenotype. This transition is confirmed by the expression of Slug, a transcriptional regulator of EMT and the down regulation of membrane E-Cadherin, a marker for epithelial phenotype. The down regulation of EpCAM and E-Cadherin with a concomitant increase in the expression of vimentin and Slug indicate the EMT nature of the CTC. Slug overexpression is shown to be an independent prognostic parameter for poor survival in colorectal carcinoma patients (et al., 2006). Also, the inventors detected the presence of β-catenin in the nucleus of the CTC that were isolated (FIG. 3D), which is an indication of active EMT cells (Brabletz et al., 2001). C-Myc accumulation in the nucleus further provides evidence for nuclear entry of β-catenin (FIG. 3D). Together these results confirm the isolation of EMT CTC using 84-1 antibody from epithelial cancer cells that are posing major drawbacks in the existing CTC detection technologies.

Figure 3E:
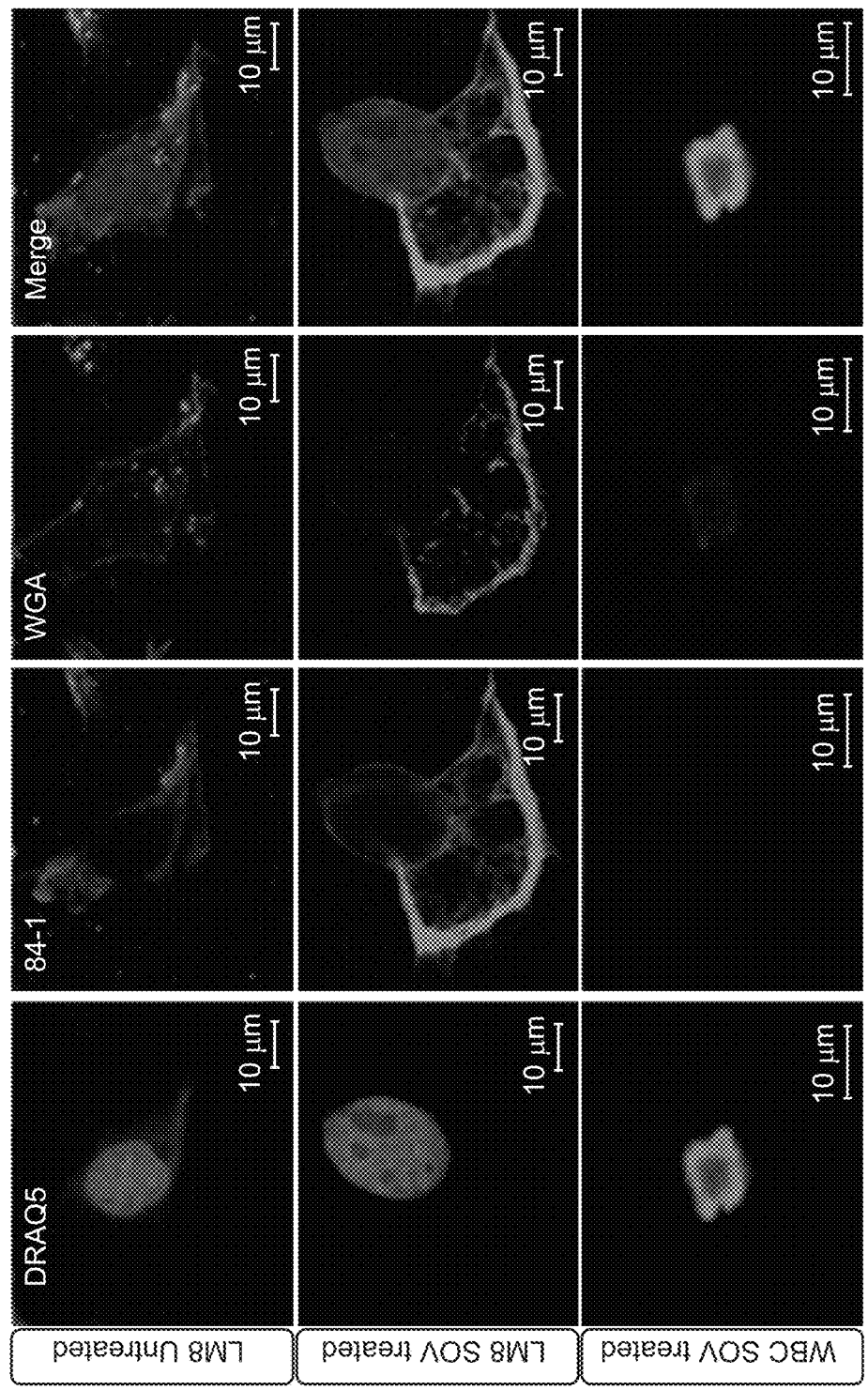
FIG. 3E: Effect of sodium orthovanadate (SOV) on LM8 and WBC. LM8 and WBCs were treated with SOV and analyzed for the expression of CSV using confocal microscopy. Cells were stained for CSV, cell surface marker WGA and nuclear stain DRAQ5. It is evident that treatment of cancer cells with SOV for 15 minutes enhances the CSV expression when compared to that of the untreated cells. There was no effect of SOV observed on WBC.
Figure 3F:
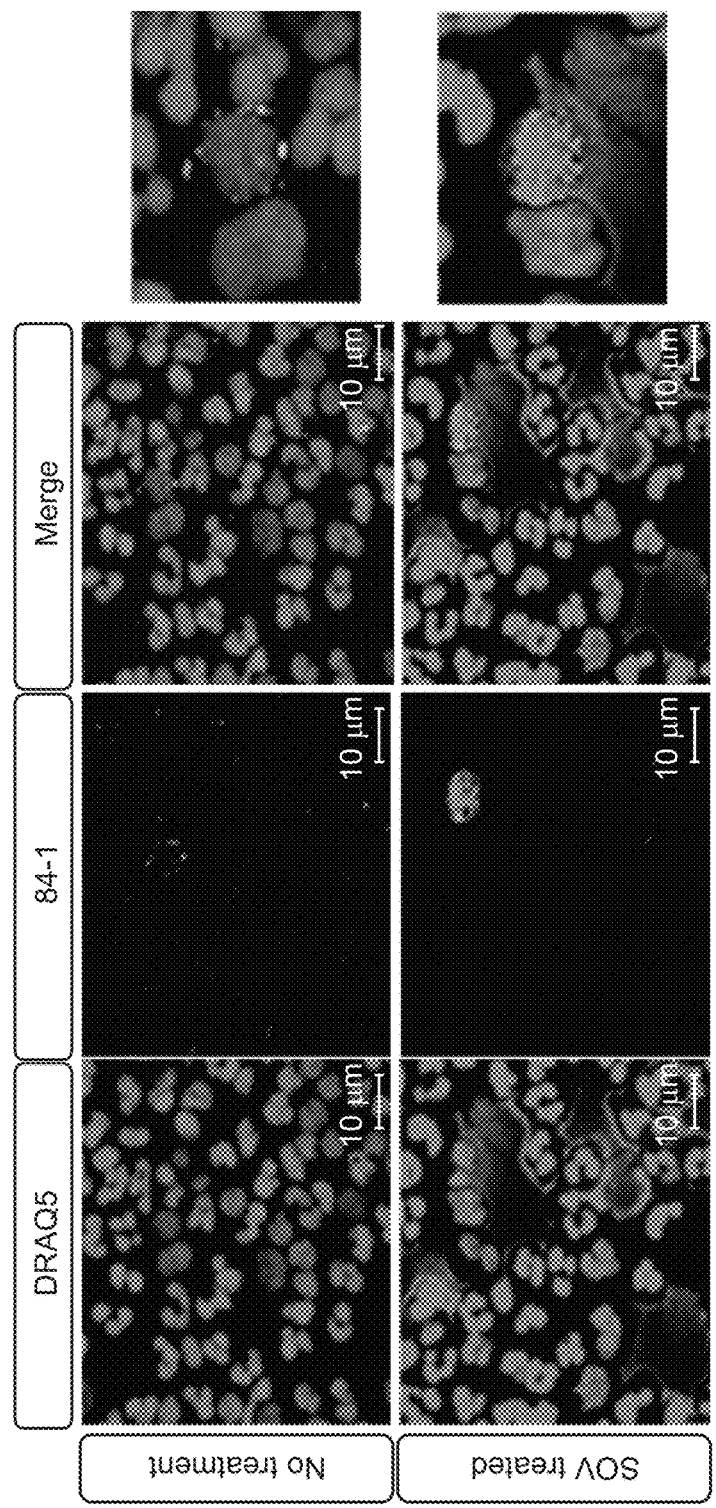
FIG. 3F: Analysis of SOV effect on patient derived CTC. Patient blood after lysis was subjected to SOV treatment and stained for vimentin using 84-1 and nuclear stain DRAQ5. SOV treatment enhanced the expression of CSV in tumor cell specifically. Scale indicates 10 µm.
Figure 7D:
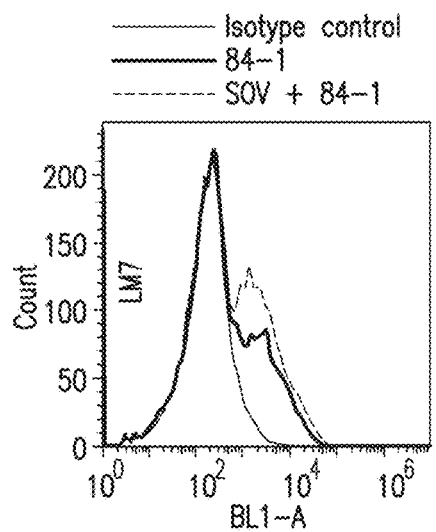
FIG. 7D: Sodium orthovanadate (SOV) treatment induces the expression of CSV on LM7 cells as visualized by flow cytometry.

Since the expression of vimentin on the cell-surface of epithelial cancers is dependent on the stage of the cancer cells, i.e. EMT stage, the inventors wanted to test if they could induce the expression of vimentin on the surface of the cancer cells using specific agents. Previous reports have suggested the translocation of vimentin to the cell-surface is phosphorylation dependent (reviewed in Satelli and Li, 2011). The inventors hypothesized that inhibiting specific phosphatases would increase phosphorylation of vimentin, thereby increasing the CSV expression. To test this hypothesis, the inventors used sodium orthovanadate (SOV), an inhibitor that inhibits specific phosphatases and increases CSV expression in cancer cells (FIG. 3E, middle panel); however, there was no change in the CSV of normal leukocytes (FIG. 3E lower panel). Furthermore, LM7 cells treated with SOV showed an increase in CSV thereby enhancing the detection of CSV with much higher efficiency (FIG. 7D). Also, the inventors tested human colon cancer blood specimens for an SOV effect that clearly indicated the increase in CSV as detectable by fluorescence microscopy (FIG. 3F). SOV can therefore be used as a CSV boosting agent thus increasing the yield of CTC, a major requirement in the detection of CTC. These results thus suggest the usage of SOV as a boosting agent to enhance the CSV expression in CTC.

CTC detection has gained a lot of momentum in clinics and is being applied in therapeutic settings; however, the uncertainties over the efficiency of CTC detection using the existing technologies calls for the discovery of new markers for CTC that can increase the efficiency of detection and aid as a valuable tool in therapeutic evaluation in patient. Herein, the inventors report the existence of vimentin on the cell surface of CTC of both non-epithelial and EMT cell types. CSV detection in CTC provides several advantages over existing marker based detection techniques. First, since there are no reports in the literature for existence of a specific marker for the detection of mesenchymal tumor derived CTC, using CSV as one specific marker highlights its superior edge over the use of a combination of markers. Second, the ability to detect EMT CTC from epithelial tumors enhances the detection abilities of existing CTC detection technologies in the market. Third, isolation of viable CTC for further molecular characterization, not just from human but also from canine and mouse models, highlights its usage as a clinical research tool.

In conclusion, the inventors discovered a CSV specific monoclonal antibody 84-1, which helps not only detection, but also isolation of viable CTCs from both epithelial and non-epithelial cancers, which can be utilized for further analysis. Enumeration of CTCs by Cell Search, Magsweeper, CTC Chips, and other technologies have revolutionized the field of CTC. However, detection utilizing these tools needs powerful biomarkers, which can aid further in the detection of CTCs in a wide variety of cancers. Since EMT transformed cells are known to escape detection by tools utilizing EpCAM and Cytokeratins as primary markers, combining with 84-1 can increase the sensitivity and reliability of these methodologies. Utilizing this antibody alone (for mesenchymal cancers) or in conjunction with the existing markers (for EMT cancers), technologies can be much more efficient in CTC detection that can improve the understanding about these metastatic precursor subpopulation and also help in providing novel diagnostics, treatment, and prognostic options based on therapeutic monitoring.

Example 3—Epitope Mapping of Mouse Monoclonal Antibodies 12-1 and 84-1 Against Vimentin The vimentin sequence was translated into 10, 12 and 15 amino acid (aa) peptides with a peptide-peptide overlap of 9, 11 and 14 aa. The peptides were spotted on a peptide array. The resulting peptide microarrays contained 1,406 different peptides as duplicates (2812 peptide spots) and were framed by Flag and HA control peptides (116 spots each).

After 10 min pre-swelling in standard buffer, pre-staining of the peptide array was done with the secondary goat anti-mouse IgG (H+L) DyLight680 antibody at a dilution of 1:5000 for 60 min at room temperature to investigate background interactions with the antigen-derived peptides that could interfere with the assays. At a scanning intensity of 7, no remarkable background interaction with the vimentin-derived peptides was observed.

Subsequent incubation of the peptide array with mouse monoclonal antibodies 12-1 and 84-1 at concentrations of 1 μg/ml in incubation buffer (PBS, pH 7.4 with 0.05% Tween 20 and 10% Rockland blocking buffer) was followed by staining with the secondary goat anti-mouse IgG (H+L) DyLight680 antibody (1:5000) and read-out at scanning intensities of 7 using a LI-COR Odyssey Imaging System. Due to the high intensity and complex staining patterns, particularly with antibody 84-1, the assays were repeated at a lower concentration of 0.2 μg/ml of antibody. Although the general intensity of the staining pattern decreased, neither the background nor the complexity of the spot pattern were reduced. An epitope-like spot pattern formed by a continuous row of neighbored peptides with a clear dependency on the various peptide lengths was not identified. Subsequently, Flag and HA controls were stained by the corresponding control antibodies.

Quantification of spot intensities and peptide annotation were done with PepSlide® Analyzer. The software algorithm breaks down fluorescence intensities of each spot into raw, foreground and background signal, and calculates the standard deviation of foreground median intensities. Based on averaged foreground median intensities, intensity maps were generated and binders in the peptide map highlighted by an intensity color code.

Averaged spot intensities of the pre-staining with the secondary antibody and the main assays with each mouse antibody against the vimentin sequence from the N-terminus to the C-terminus were plotted to visualize overall spot intensities and signal to noise ratios. The intensity plots were correlated with peptide and intensity maps as well as with visual inspection of the microarray scan to identify consensus motifs and distinctive peptides that interacted with the antibody samples.

Figure 11:
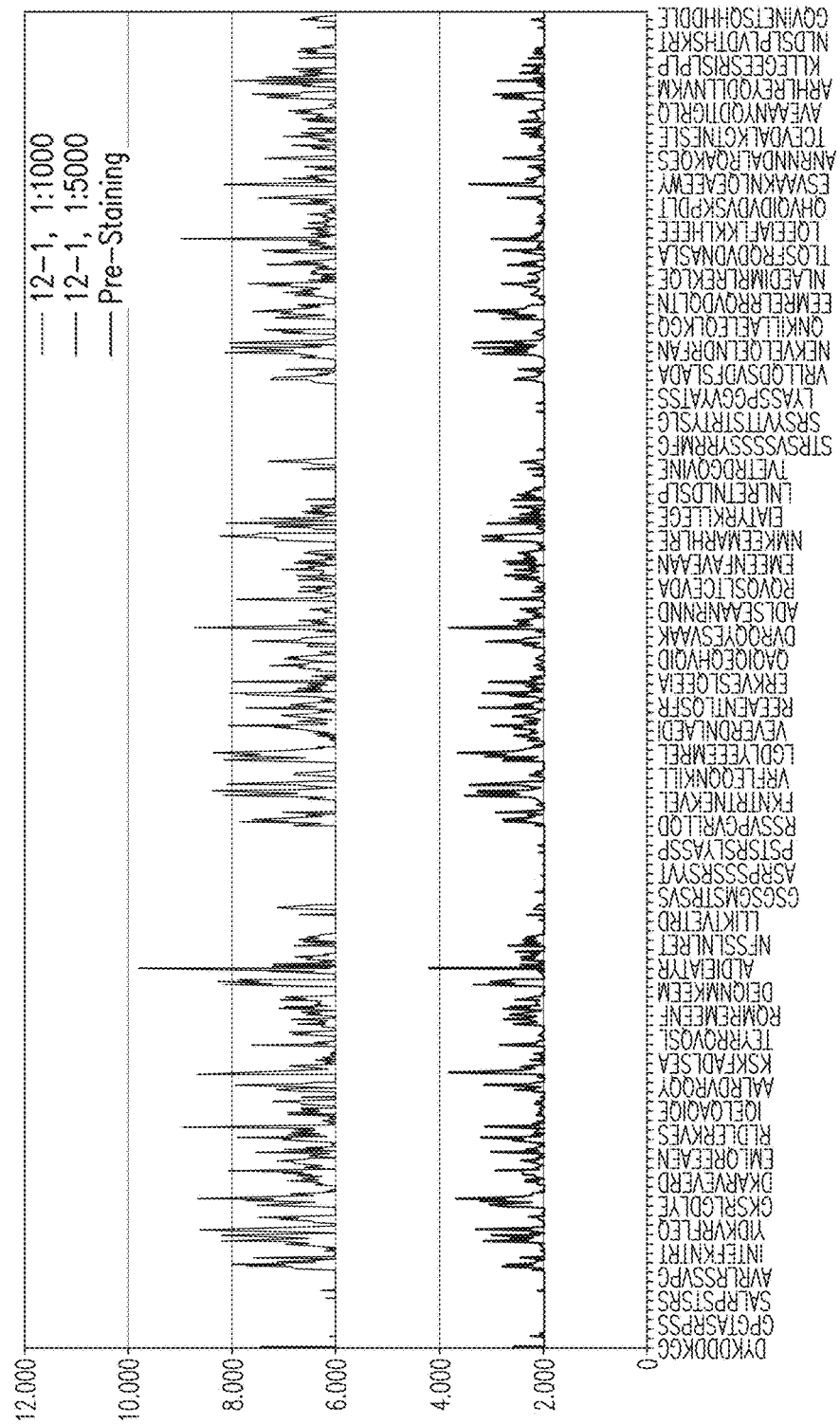
FIG. 11: Antibody 12-1 intensity plot. Data quantification was followed by generation of peptide and intensity maps as well as of intensity plots for the pre-staining (bottom plot) and the main assays (1:5000 middle plot; 1:1000 top plot) with the 10 aa peptides on left, the 12 aa peptides in the middle and the 15 aa peptides on right. (SEQ ID NOs: 9-65, left to right)
Figure 12:
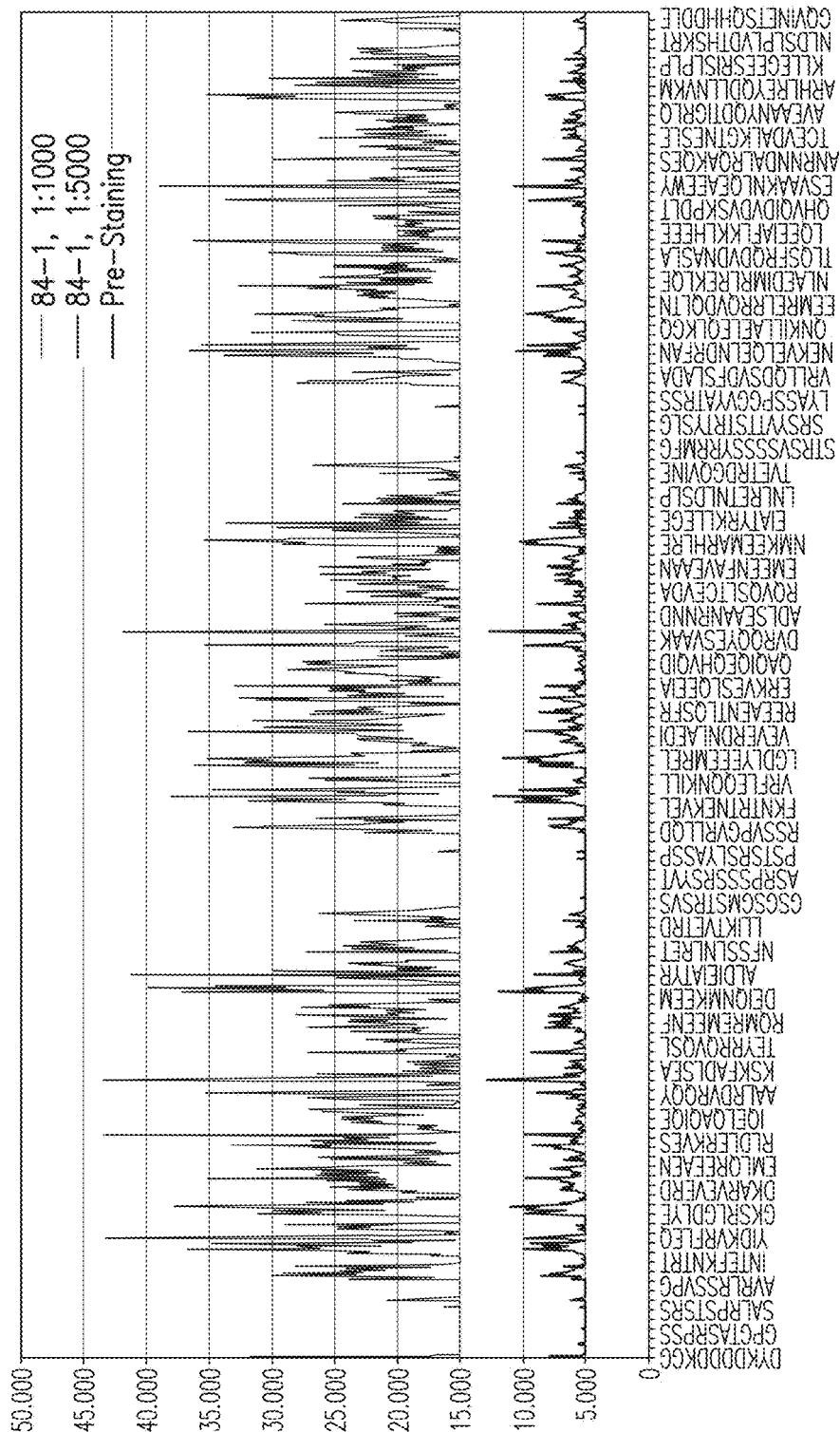
FIG. 12: Antibody 84-1 intensity plot. Data quantification was followed by generation of peptide and intensity maps as well as of intensity plots for the pre-staining (bottom plot) and the main assays (1:5000—middle plot; 1:1000—top plot) with the 10 aa peptides on left, the 12 aa peptides in the middle and the 15 aa peptides on right. (SEQ ID NOs: 9-65, left to right)
Figure 13:
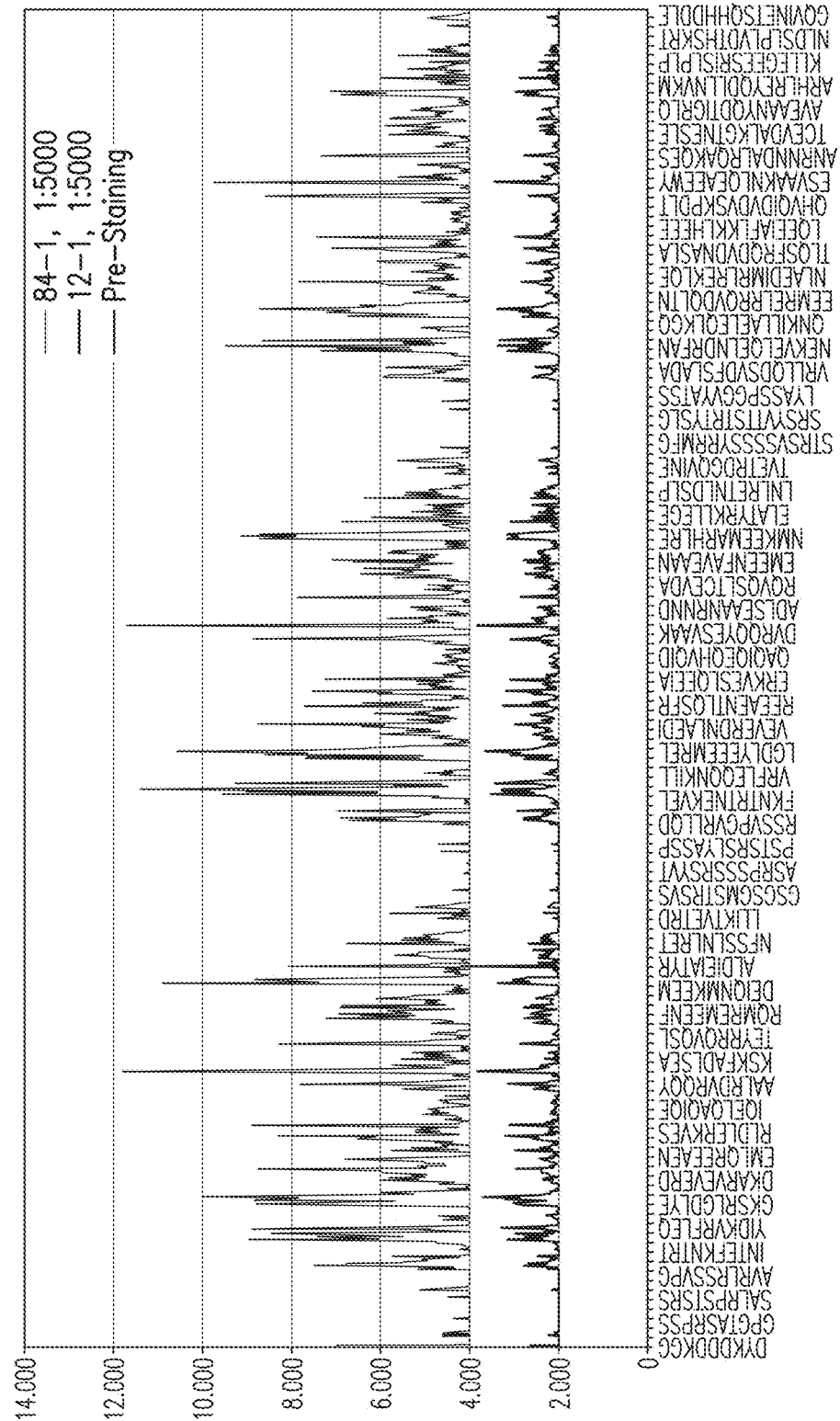
FIG. 13: Combined antibodies 12-1 and 84-1 intensity plots. Comparison of the intensity plots of mouse monoclonal antibodies 12-1 (middle plot) and 84-1 (top plot) revealed the pronounced similarity of both samples with the 10 aa peptides on left, the 12 aa peptides in the middle and the 15 aa peptides on right. (SEQ ID NOs: 9-65, left to right)

In accordance with the microarray scans and the intensity map, a complex and noisy response was observed due to a strong cross-reactivity of antibody 12-1 (FIG. 11) and antibody 84-1 (FIG. 12) without a clear epitope-like pattern. Comparison of the intensity plots of mouse monoclonal antibodies 12-1 (1 ug/mL) and 84-1 (0.2 ug/mL) revealed the pronounced similarity of both samples (FIG. 13). Both antibodies apparently exhibited a similar cross-reactivity with approximately doubled spot intensities with antibody 84-1, and no epitope-like spot pattern formed by neighbored peptides with an overlapping consensus motif.

Figure 14:
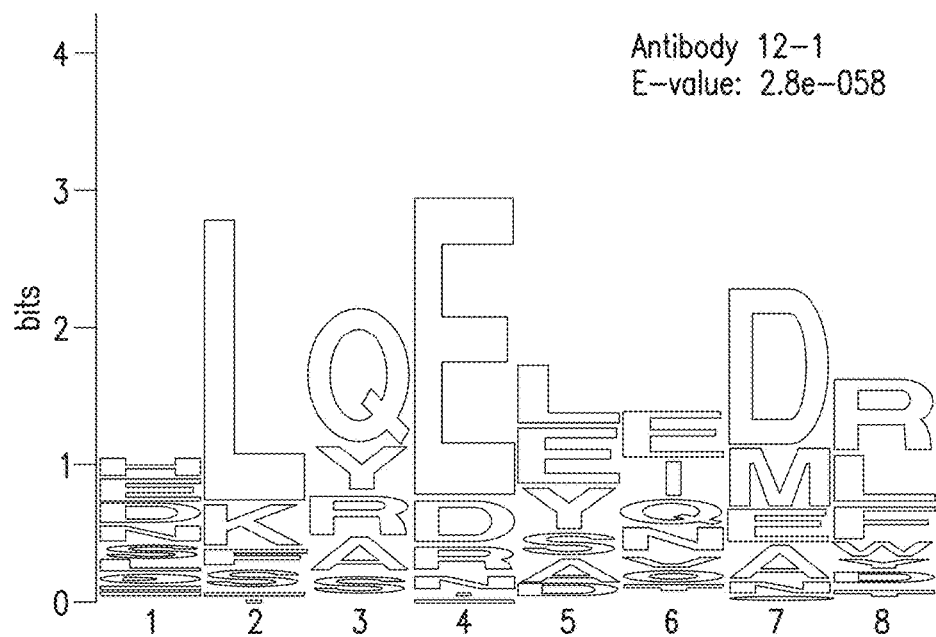
FIG. 14: MEME motif for antibody 12-1.
Figure 15:
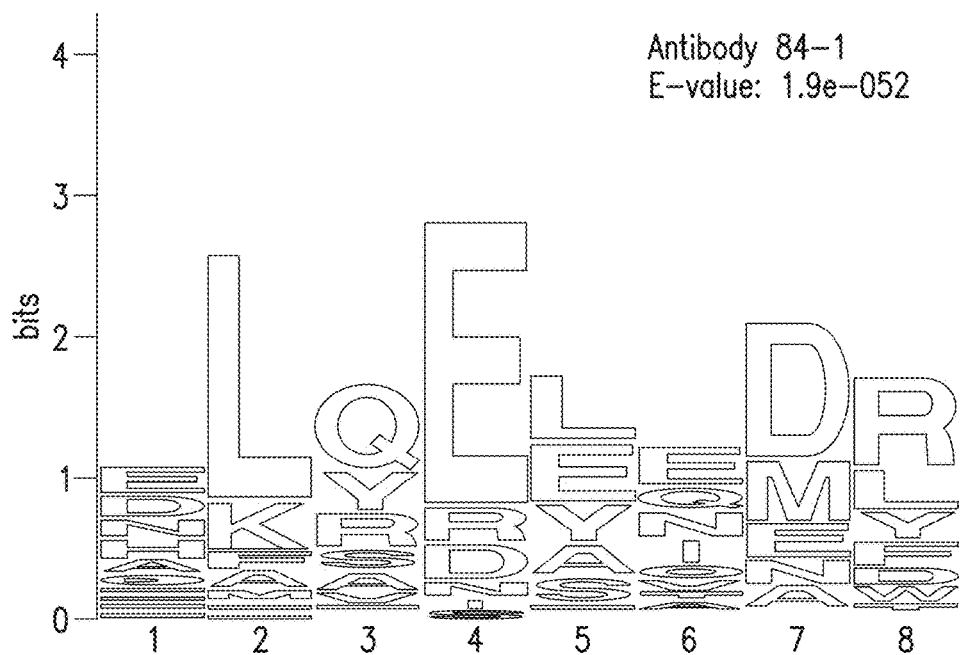
FIG. 15: MEME motif for antibody 84-1.

The identification of possible raw motifs and amino acid preferences of both antibodies were supported by MEME Suite (Motif-based sequence analysis tools) (FIGS. 14 and 15). For MEME analysis, the top 100 peptides of each assay were selected and a minimal motif length of only two amino acids was defined. The resulting E-values correspond to the statistical significance of a consensus motif with the given log likelihood ratio (or higher), and with the same width and site count, that one would find in a similarly sized set of random sequences. An E-value of 1 would be expected for the identification of a certain motif in a set of random peptides by chance; decreasing E-values correlate with increasing statistical significance.

MEME analysis underlined the pronounced similarity of both antibodies 12-1 and 84-1 with a top motif xLQE[LE]E[DM]R and a very high statistical significance. The samples showed a clear preference for acidic amino acids D and E as well as for hydrophobic amino acids M, F, A and particularly L. MEME analysis further indicated a preferred spacer of one amino acid between hydrophobic amino acid L and acidic amino acids D or E. Based on this, there are several possible sub-motifs, including LQE, QEL, QEE, QE[xx]E[xx]R, E[x]E[M]R, L[x]E, and xLxExxD.

Example 4—Detection of CTC in Blood From Cancer Patients

Figure 9:
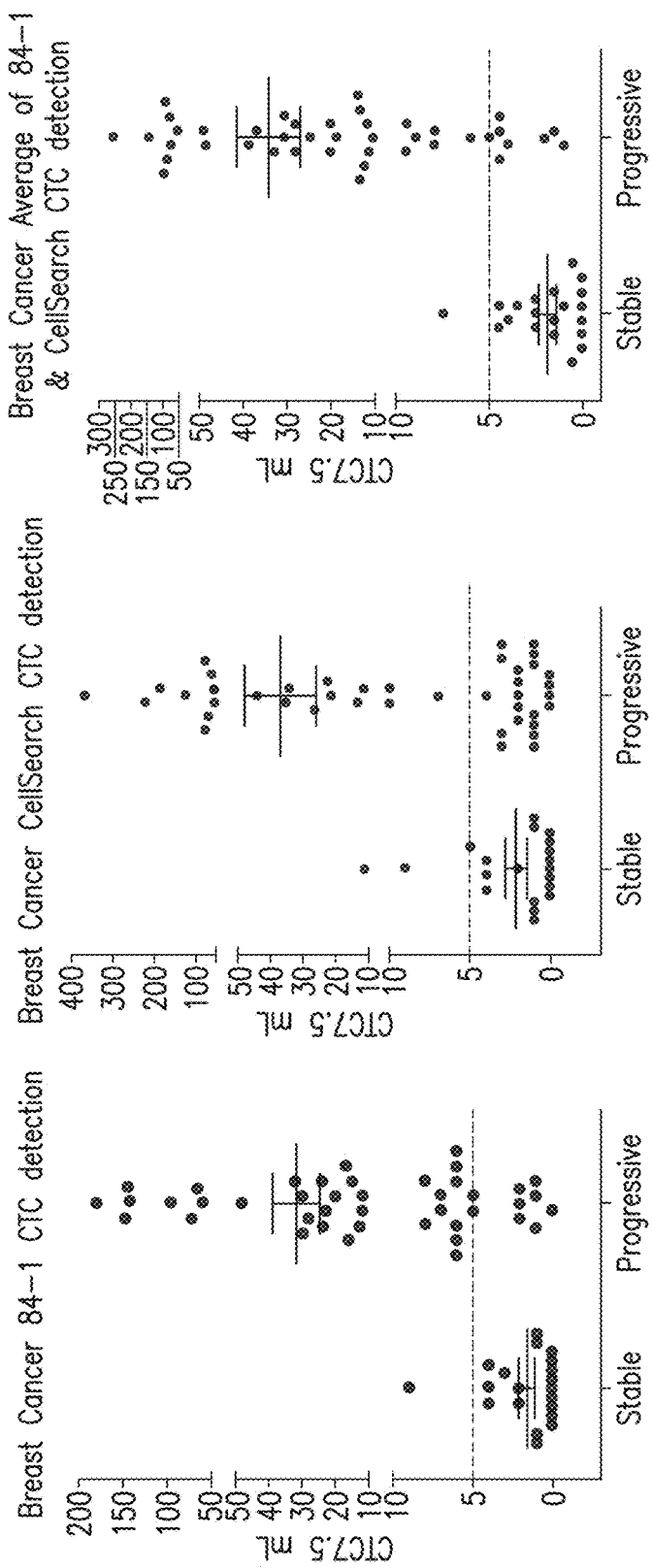
FIG. 9: Comparison of breast cancer CTC detection methods using 84-1, CellSearch, and 84-1+CellSearch. One tube of blood from each metastatic breast cancer patient was used to enumerate CTC by 84-1 method (FIG. 9A) and CellSearch method (FIG. 9B). Average numbers of CTC were calculated from both 84-1 and CellSearch methods (FIG. 9C). These patients were classified into stable (responding to therapy) and progressive (not responding to therapy, show tumor progression) populations.

In order to test the ability to detect CTCs in the blood of breast cancer patients, two tubes of blood (7.5 mL each) were obtained from 62 patients with metastatic breast cancer. One tube each was used to enumerate CTC by the 84-1 method (FIG. 9A) and the CellSearch method (FIG. 9B). Average numbers of CTC were calculated from both the 84-1 and CellSearch methods to generate a combined methods average (FIG. 9C). The patients were classified into stable (responding to therapy) and progressive (not responding to therapy, show tumor progression) populations. Sensitivity and specificity of detection were calculated for each method: 84-1 (83.3% and 95%, respectively), CellSearch (50% and 85%, respectively), and combined methods average (83.3% and 95%, respectively).

Figure 10:
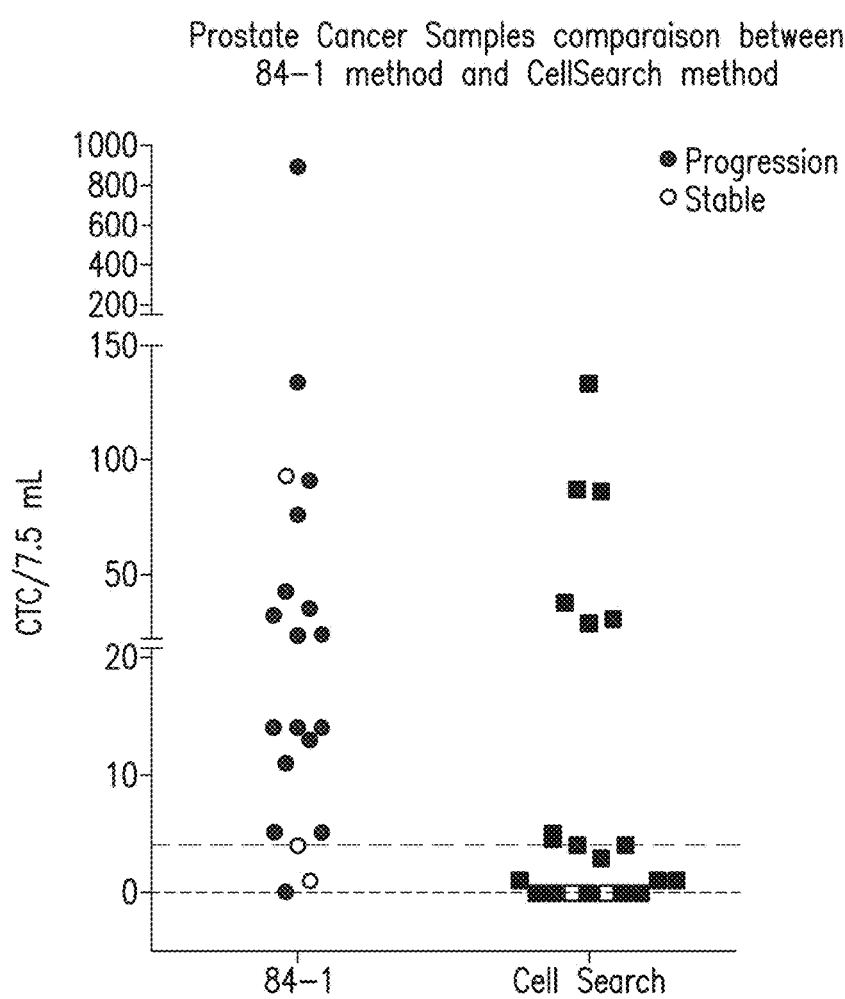
FIG. 10: Comparison of prostate cancer CTC detection methods using 84-1 and CellSearch. One tube of blood from each prostate cancer patient was used to enumerate CTC by 84-1 method and CellSearch method. These patients were classified into stable (responding to therapy) and progressive (not responding to therapy, show tumor progression) populations.

In order to test the ability to detect CTCs in the blood of prostate cancer patients, two tubes of blood (7.5 mL each) were obtained from 21 patients with metastatic prostate cancer. One tube each was used to enumerate CTC by the 84-1 method and the CellSearch method (FIG. 10). The patients were classified into stable (responding to therapy) and progressive (not responding to therapy, show tumor progression) populations. Sensitivity of detection was calculated for each method: 84-1 (95%) and CellSearch (50%). Specificity of detection was not calculated due to the limited number of samples available.

TABLE 1

Cell-surface vimentin expression in different cell lines.

| Cell Line | Cell-surface Vimentin |
|---|---|
| Breast | |
| MCF-7 (H) | + |
| SKBR3 (H) | + |
| BT-474 (H) | − |
| MDA-MB-231 (H) | + |
| MDA-MB-453 (H) | + |
| MDA-MB-458 (H) | ++ |
| EMT-6 (M) | − |
| 4T1 (M) | + |
| Liver | |
| SNU398 (H) | − |
| HEP3B (H) | − |
| SNU 499 (H) | − |
| AMC14 (M) | ++ |
| Brain | |
| SKNAS (H) | ++ |
| SKNBE2 (H) | +++ |
| SK-N-SH (H) | − |
| NGP (H) | + |
| CHP134 (H) | − |
| SH-SY5Y (H) | ++ |
| LAN5 (H) | ++ |
| KCN (H) | + |
| DBT (M) | + |
| U87 MG (H) | − |
| U251 (H) | + |
| Colon | |
| DLD-1 (H) | ++ |
| GEO (H) | ++ |
| OS-187 (H) | ++ |
| SW620 (H) | + |
| SW480 (H) | + |
| HCT-116 (H) | + |
| HT-29 (H) | ++ |
| Caco-2 (H) | + |
| CT-26 (M) | + |
| Bone | |
| OS-25 (H) | ++ |
| HOS (H) | ++ |
| MG-263 (H) | ++ |
| LM7 (H) | + |
| SAOS-2 (H) | + |
| OS25 (H) | + |
| OS-O (H) | ++ |
| OS-D (H) | + |
| U2OS (H) | + |
| CCH-OSD (H) | + |
| K7 (M) | ++ |
| K7M2 (M) | +++ |
| DUNN (M) | + |
| LM8 (M) | +++ |
| Bladder | |
| RT4V6 (H) | + |
| J82 (H) | − |
| T24 (H) | ++ |
| UC9 (H) | − |
| Pancreas | |
| PANC-1 (H) | ++ |
| MiaPACA-2 (H) | + |
| Other | |
| HeLa (H) | − |
| PC-3M (H) | − |
| B16F10 (M) | − |
| FBL3 (M) | +++ |
| SCCVII (M) | + |

(H): Human, (M): Mouse.
Cell-surface vimentin was scored using flow cytometric analysis by measuring mean fluorescence intensity of CSV.
"−": Not detectable, "+, ++, +++": <2, <4, >4 fold presence compared to isotype control.

TABLE 2

Cell-surface vimentin (CSV) evaluation in primary osteosarcoma cell lines.

| Cell Line | Disease Variant | Metastasis | CSV |
| --- | --- | --- | --- |
| OST-DL-390 | Osteosarcoma | No | − |
| OST-DL-391 | Osteosarcoma | Yes to lung | + |
| OST-DL-393 | Osteosarcoma | Yes to lung | + |
| OST-DL-396a | Osteosarcoma | Yes to brain | ++ |
| OST-DL-399 | Osteosarcoma | No | − |

MFI: Mean fluorescence intensity
(−) No MFI change,
(+) <2 fold MFI increase,
(++) >2 fold MFI increase

TABLE 3

CTC enumeration in different cancer patient samples.

| Patient Number | Tumor Location | Disease Variant | Disease Status | Pretreatment | CTCs/mL |
| --- | --- | --- | --- | --- | --- |
| Osteosarcoma | | | | | |
| OB1 | Humerus | High Grade | Metastatic to LN | Chemo | 8 |
| OB2 | Tibia | Well-diff, intramedullary | Primary | None | 0 |
| OB3 | Knee, Lung | High Grade Osteoblastic | Metastatic to lung | Chemo | 3 |
| OB4 | Femur, Lung | Fibroblastic, giant cell-rich | Metastatic to lung | Chemo | 4 |
| OB5 | Femur | Fibroblastic, giant cell-rich | Metastatic to lung | Chemo | 6 |
| UPS | | | | | |
| UP1 | Back | No viable tumor | Primary | XRT | 1 |
| UP2 | Retroperitoneum | No viable tumor | Primary | Chemo, XRT | 0 |
| UP3 | Chest wall | | Primary | XRT | 2 |
| UP4 | Chest wall | | Locally recurrent | None | 4 |
| UP5 | Knee | No tumor | Residual primary | XRT | 2 |
| UP6 | Pelvis, liver, lung | | Metastatic to liver, lung | Chemo, XRT | 6 |
| Leiomyosarcoma | | | | | |
| LM1 | Pelvis | Uterine | Locally recurrent | Chemo | 4 |
| LM2 | Arm, lung | | Metastatic to lung | Chemo | 8* |
| LM3 | Abdomen/pelvis | Uterine | Primary | Chemo | 5 |
| Liver | | | | | |
| L1 | Liver | Recurrent HCC | LI detected | Chemo | 5 |
| Colon | | | | | |
| CRC1 | Colon | Invasive adenocarcinoma | Metastatic to liver & lung | Chemo | 8 |
| CRC2 | Colorectal | Invasive adenocarcinoma | Metastatic to liver & lung | Chemo | 12 |
| CRC3 | Colon | Mucinous adenocarcinoma | Primary | Chemo | 4 |
| CRC4 | Colon | Colon cancer | Metastatic | Chemo | 8 |
| CRC5 | Colon | Adenocarcinoma | Metastatic to liver & lung | Chemo | 16 |
| CRC6 | Colon | Adenocarcinoma | Metastatic to lung, bone, brain, muscle | Chemo | 12 |

LN: Lymph nodes, HCC: Hepatocellular carcinoma, LI: Lymphovascular invasion, Chemo: Chemotherapy, XRT: External radiation therapy, UPS: Unidentified pleomorphic sarcoma,
*detection based on live cell imaging.

TABLE 4

CTC enumeration in mouse with spontaneous tumors.

| Mouse Number | Disease Variant | Metastasis | CTCs/mL |
|---|---|---|---|
| DD554 | Normal | No | 0 |
| DD616 | Lymphoma | No | 0 |
| DD596 #3 | Mammary lymphoma | No | 0 |
| DD705 | Thymus | No | 0 |
| DD732 | Osteosarcoma | No | 1 |
| DD674 | Sarcoma | No | 1 |
| DD729 | Thymus | No | 1 |
| DD446 | Liver tumor | Yes to lymph nodes | 2 |
| DD60 | Intestine | No | 2 |
| DD753 | Osteosarcoma | No | 3 |
| DD2992 | Liver tumor | No | 4 |
| DD596 #77 | Ovarian | No | 7 |
| DD701 | Thymus | Yes to liver | 7 |
| DD636 | Thymus | Yes to liver | 9 |
| DD637 | Thymus | Yes to liver | 9 |
| DD730 | Thymus | Yes to lung | 31 |
| DD43 | Osteosarcoma | Yes to lung | 45 |
| DD592 | Osteosarcoma | Yes to lung | 56 |
| DD470 | Osteosarcoma | Yes to lung | 80 |
| DD93 | Intestine | Yes | 154 |
| DD493 | Haemangiosarcoma | Yes to liver, lung | 175 |
| DD596 #4 | Osteosarcoma | Yes to lung | 258 |

TABLE 5

Evaluation of 84-1 sensitivity and specificity using spiking analysis.

| Method | PBMC | Spiked | Extracted | Background |
|---|---|---|---|---|
| Sensitivity | | | | |
| 84-1 pull | 10 × 10⁶ | 2 | 1 | 0 |
| 84-1 pull | 10 × 10⁶ | 5 | 3 | 0 |
| 84-1 pull | 10 × 10⁶ | 10 | 7 | 0 |
| Specificity | | | | |
| 84-1 pull | 10 × 10⁶ | 5 | 3 | 0 |
| 84-1 pull | 20 × 10⁶ | 5 | 2 | 0 |
| 84-1 pull | 20 × 10⁶ | 5 | 3 | 0 |

TABLE 6

Evaluation of 12-1 sensitivity and specific using spiking analysis.

| Method | PBMC | Spiked | Extracted | Background |
|---|---|---|---|---|
| 12-1 pull | 10 × 10⁶ | 5 | 2 | 0 |
| 12-1 pull | 10 × 10⁶ | 5 | 1 | 0 |
| 12-1 pull | 10 × 10⁶ | 5 | 2 | 0 |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bhattacharya et al., Recruitment of vimentin to the cell surface by beta3 integrin and plectin mediates adhesion strength, *J. Cell Sci.*, 122:1390-1400, 2009.

Brabletz et al., Variable beta-catenin expression in colorectal cancers indicates tumor progression driven by the tumor environment, *Proc. Natl. Acad. Sci. U.S.A.*, 98:10356-10361, 2001.

Brabletz et al., Opinion: migrating cancer stem cells—an integrated concept of malignant tumour progression, *Nat. Rev. Cancer*, 5:744-749, 2005.

Cutrera et al., Discovery of a linear peptide for improving tumor targeting of gene products and treatment of distal tumors by IL-12 gene therapy. *Mol. Ther.*, 19:1468-1477, 2011.

Gasch et al., Heterogeneity of epidermal growth factor receptor status and mutations of KRAS/PIK3CA in circulating tumor cells of patients with colorectal cancer, *Clin. Chem.*, 59:252-260, 2013.

Huet et al., SC5 mAb represents a unique tool for the detection of extracellular vimentin as a specific marker of Sezary cells, *J. Immunol.*, 176:652-659, 2006.

Mackall et al., Focus on sarcomas, *Cancer Cell*, 2:175-178, 2002.

Modest et al., Clinical characterization of patients with metastatic colorectal cancer depending on the KRAS status, *Anticancer Drugs*, 22:913-918, 2011.

TABLE 7

VH and VL CDR regions of 84-1.

| Heavy Chain Sequence | | | Light Chain Sequence | | |
|---|---|---|---|---|---|
| CDR1 | CDR2 | CDR3 | CDR1 | CDR2 | CDR3 |
| Amino acid sequence | | | Amino acid sequence | | |
| GFSLTRYGVH (SEQ ID NO: 3) | VIWSGGSTDYNAAF IS (SEQ ID NO: 4) | RSYYYAMDY (SEQ ID NO: 5) | RSSQSIVHRIGNTY LE (SEQ ID NO: 6) | KVSNRFS (SEQ ID NO: 7) | FQGSHVPLT (SEQ ID NO: 8) |
| QVQLKQSGPGLVQPSQSLSITCTVS<u>GFSLTRYGVH</u>WVRQSP GKGLEWLG<u>VIWSGGSTDYNAAFIS</u>RLSFSKDNSKSQVFFKM NSLQANDTAIYYCAR<u>RSYYYAMDY</u>WGQGTSVTVS (SEQ ID NO: 1) | | | DVLMTQTPLSLPVSLGDQASISC<u>RSSQSIVHRIGNTYLE</u>WY LQKPGQSPKLLIY<u>KVSNRFS</u>GVPDRFSGSGSGTDFTLKISR VEAEDLGVYYC<u>FQGSHVPLT</u>FGAGTKLEL (SEQ ID NO: 2) | | |

Moisan and Girard, Cell surface expression of intermediate filament proteins vimentin and lamin B1 in human neutrophil spontaneous apoptosis, *J. Leukoc. Biol.,* 79:489-498, 2006.

Mor-Vaknin et al., Vimentin is secreted by activated macrophages, *Nat. Cell Biol.,* 5:59-63, 2003.

Pantel and Brakenhoff, Dissecting the metastatic cascade, *Nat. Rev. Cancer,* 4:448-456, 2004.

Parkinson et al., Considerations in the development of circulating tumor cell technology for clinical use, *J. Transl. Med.,* 10:138, 2012.

Powell et al., Single cell profiling of circulating tumor cells: transcriptional heterogeneity and diversity from breast cancer cell lines, *PLoS One,* 7:e33788, 2012.

Satelli and Li, Vimentin in cancer and its potential as a molecular target for cancer therapy, *Cell Mol. Life Sci.,* 68:3033-3046, 2011.

Shioiri et al., Slug expression is an independent prognostic parameter for poor survival in colorectal carcinoma patients, *Br. J. Cancer,* 94:1816-1822, 2006.

Sieuwerts et al., Anti-epithelial cell adhesion molecule antibodies and the detection of circulating normal-like breast tumor cells, *J. Natl. Cancer Inst.,* 101:61-66, 2009. 0

Tortola et al., Discordance between K-ras mutations in bone marrow micrometastases and the primary tumor in colorectal cancer, *J. Clin. Oncol.,* 19:2837-2843, 2001.

The invention claimed is:

1. An isolated antibody-cell complex comprising an isolated and captured complex of a monoclonal antibody or an antigen binding fragment thereof bound to vimentin on the cell surface of a non-permeabilized metastatic tumor cell, wherein the metastatic tumor cell is a circulating metastatic tumor cell of a solid tumor, wherein the antibody or antigen binding fragment comprises:
   (a) a first VH CDR identical to SEQ ID NO: 3;
   (b) a second VH CDR identical to SEQ ID NO: 4;
   (c) a third VH CDR identical to SEQ ID NO: 5;
   (d) a first VL CDR identical to SEQ ID NO: 6;
   (e) a second VL CDR identical to SEQ ID NO: 7; and
   (f) a third VL CDR identical to SEQ ID NO: 8.

2. The complex of claim 1, wherein the antibody or antigen binding fragment comprises a $V_H$ domain at least 95% identical to the $V_H$ domain of 84-1 (SEQ ID NO: 1) and a $V_L$ domain at least 95% identical to the $V_L$ domain of 84-1 (SEQ ID NO: 2).

3. The complex of claim 1, wherein the antibody or antigen binding fragment comprises a $V_H$ domain identical to the $V_H$ domain of 84-1 (SEQ ID NO: 1) and a $V_L$ domain identical to the $V_L$ domain of 84-1 (SEQ ID NO: 2).

4. The complex of claim 1, in a composition further comprising a protein tyrosine phosphatase inhibitor to stabilize the complex.

5. The complex of claim 4, wherein the protein tyrosine phosphatase inhibitor is sodium orthovanadate, dephostatin, mpV(pic), phenylarsine oxide, sodium stibogluconate, BAY U6751, a tyrosine phosphatase inhibitor cocktail (including sodium vanadate, sodium molybdate, sodium tartrate, and imidazole), and RK-682.

6. The complex of claim 1, wherein the tumor cell is an epithelial tumor or a mesenchymal tumor.

7. The complex of claim 1, bound to a surface.

8. The complex of claim 7, wherein the surface is the surface of test tube, a microtiter well, a slide or a chip.

9. The complex of claim 7, in a composition further comprising an enzyme and a substrate for the enzyme.

10. The complex of claim 9, wherein the enzyme is horseradish peroxidase (HRP) or alkaline phosphatase (AP).

11. The complex of claim 1, wherein a reporter or effector molecule is bound to the complex.

12. The complex of claim 9, wherein the substrate is 3,3',5,5'-Tetramethylbenzidine or 3,3'-Diaminobenzidine.

13. The complex of claim 1, wherein the antigen binding fragment is an Fab', a F(ab')2, a F(ab') 3, a monovalent scFv, or a bivalent scFV.

14. The complex of claim 9, wherein the substrate is 3,3',5,5'-Tetramethylbenzidine or 3,3'-Diaminobenzidine.

15. The antibody-cell complex of claim 1, wherein the complex is formed ex vivo or in vitro.

16. The complex of claim 11, wherein the reporter or effector molecule is an enzyme, a florescence-linked CSV binding antibody, or an anti-mouse IgG-linked enzyme.

* * * * *

UNITED STATES PATENT AND TRADEMARK OFFICE
CERTIFICATE OF CORRECTION

| | |
|---|---|
| PATENT NO. | : 10,329,353 B2 |
| APPLICATION NO. | : 14/772655 |
| DATED | : June 25, 2019 |
| INVENTOR(S) | : Satelli et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 99 days.

Signed and Sealed this
Thirty-first Day of December, 2019

Andrei Iancu
*Director of the United States Patent and Trademark Office*

SEQUENCE LISTING

```
<160> NUMBER OF SEQ ID NOS: 65

<210> SEQ ID NO 1
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Arg Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Phe Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Arg Ser Tyr Tyr Tyr Ala Met Asp Tyr Trp Gly Gln Gly Thr Ser
            100                 105                 110

Val Thr Val Ser
        115

<210> SEQ ID NO 2
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 2

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Arg
            20                  25                  30

Ile Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Leu Gly Val Tyr Tyr Cys Phe Gln Gly
            85                  90                  95

Ser His Val Pro Leu Thr Phe Gly Ala Gly Thr Lys Leu Glu Leu
            100                 105                 110

<210> SEQ ID NO 3
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 3

Gly Phe Ser Leu Thr Arg Tyr Gly Val His
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 4

Val Ile Trp Ser Gly Gly Ser Thr Asp Tyr Asn Ala Ala Phe Ile Ser
1               5                   10                  15

<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

Arg Ser Tyr Tyr Tyr Ala Met Asp Tyr
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 6

Arg Ser Ser Gln Ser Ile Val His Arg Ile Gly Asn Thr Tyr Leu Glu
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

Lys Val Ser Asn Arg Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide
```

```
<400> SEQUENCE: 8

Phe Gln Gly Ser His Val Pro Leu Thr
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Asp Tyr Lys Asp Asp Asp Asp Lys Gly Gly
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Gly Pro Gly Thr Ala Ser Arg Pro Ser Ser
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Ser Ala Leu Arg Pro Ser Thr Ser Arg Ser
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Ala Val Arg Leu Arg Ser Ser Val Pro Gly
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Ile Asn Thr Glu Phe Lys Ile Asn Thr Arg Thr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14
```

Tyr Ile Asp Lys Val Arg Phe Leu Glu Gln
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Gly Lys Ser Arg Leu Gly Asp Leu Tyr Glu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide

<400> SEQUENCE: 16

Asp Lys Ala Arg Val Glu Val Glu Arg Asp
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Glu Met Leu Gln Arg Glu Glu Ala Glu Asn
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Arg Leu Asp Leu Glu Arg Lys Val Glu Ser
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide

<400> SEQUENCE: 19

Ile Gln Glu Leu Gln Ala Gln Ile Gln Glu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Ala Ala Leu Arg Asp Val Arg Gln Gln Tyr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Lys Ser Lys Phe Ala Asp Leu Ser Glu Ala
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

Thr Glu Tyr Arg Arg Gln Val Gln Ser Leu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Arg Gln Met Arg Glu Met Glu Glu Asn Phe
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Asp Glu Ile Gln Asn Met Lys Glu Glu Met
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Ala Leu Asp Ile Glu Ile Ala Thr Tyr Arg
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Asn Phe Ser Ser Leu Asn Leu Arg Glu Thr

```
1               5                   10
```

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide

<400> SEQUENCE: 27

```
Leu Leu Ile Lys Thr Val Glu Thr Arg Asp
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Synthetic peptide

<400> SEQUENCE: 28

```
Gly Ser Gly Ser Gly Met Ser Thr Arg Ser Val Ser
1               5                   10
```

<210> SEQ ID NO 29
<211> LENGTH: 12
<212> TYPE: PRT
<213> ORGANISM: Artificial Sequence
<220> FEATURE:
<223> OTHER INFORMATION: Synthetic peptide

<400> SEQUENCE: 29

```
Ala Ser Arg Pro Ser Ser Ser Arg Ser Tyr Val Thr
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: Synthetic peptide

<400> SEQUENCE: 30

```
Pro Ser Thr Ser Arg Ser Leu Tyr Ala Ser Ser Pro
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide

<400> SEQUENCE: 31

```
Arg Ser Ser Val Pro Gly Val Arg Leu Leu Gln Asp
1               5                   10
```

<210> SEQ ID NO 32
<211> LENGTH: 12
<212> TYPE: PRT
<213> ORGANISM: Artificial Sequence
<220> FEATURE:
<223> OTHER INFORMATION: Synthetic peptide

<400> SEQUENCE: 32

```
Phe Lys Asn Thr Arg Thr Asn Glu Lys Val Glu Leu
1               5                   10
```

```
<210> SEQ ID NO 33
<211> LENGTH: 12
<212> TYPE: PRT
<213> ORGANISM: Artificial Sequence
<220> FEATURE:
<223> OTHER INFORMATION: Synthetic peptide

<400> SEQUENCE: 33

Val Arg Phe Leu Glu Gln Gln Asn Lys Ile Leu Leu
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic peptide

<400> SEQUENCE: 34

Leu Gly Asp Leu Tyr Glu Glu Glu Met Arg Glu Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide

<400> SEQUENCE: 35

Val Glu Val Glu Arg Asp Asn Leu Ala Glu Asp Ile
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic peptide

<400> SEQUENCE: 36

Arg Glu Glu Ala Glu Asn Thr Leu Gln Ser Phe Arg
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic peptide

<400> SEQUENCE: 37

Glu Arg Lys Val Glu Ser Leu Gln Glu Glu Ile Ala
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic peptide

<400> SEQUENCE: 38

Gln Ala Gln Ile Gln Glu Gln His Val Gln Ile Asp
1               5                   10
```

<210> SEQ ID NO 39
<211> LENGTH: 12
<212> TYPE: PRT
<213> ORGANISM: Artificial Sequence
<220> FEATURE:
<223> OTHER INFORMATION: Synthetic peptide

<400> SEQUENCE: 39

Asp Val Arg Gln Gln Tyr Glu Ser Val Ala Ala Lys
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic peptide

<400> SEQUENCE: 40

Ala Asp Leu Ser Glu Ala Ala Asn Arg Asn Asn Asp
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic peptide

<400> SEQUENCE: 41

Arg Gln Val Gln Ser Leu Thr Cys Glu Val Asp Ala
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic peptide

<400> SEQUENCE: 42

Glu Met Glu Glu Asn Phe Ala Val Glu Ala Ala Asn
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic peptide

<400> SEQUENCE: 43

Asn Met Lys Glu Glu Met Ala Arg His Leu Arg Glu
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic peptide

<400> SEQUENCE: 44

Glu Ile Ala Thr Tyr Arg Lys Leu Leu Glu Gly Glu
1               5                   10

```
<210> SEQ ID NO 45
<211> LENGTH: 12
<212> TYPE: PRT
<213> ORGANISM: Artificial Sequence
<220> FEATURE:
<223> OTHER INFORMATION: Synthetic peptide

<400> SEQUENCE: 45

Leu Asn Leu Arg Glu Thr Asn Leu Asp Ser Leu Pro
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic peptide

<400> SEQUENCE: 46

Thr Val Glu Thr Arg Asp Gly Gln Val Ile Asn Glu
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Synthetic peptide

<400> SEQUENCE: 47

Ser Thr Arg Ser Val Ser Ser Ser Tyr Arg Arg Met Phe Gly
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic peptide

<400> SEQUENCE: 48

Ser Arg Ser Tyr Val Thr Thr Ser Thr Arg Thr Tyr Ser Leu Gly
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Synthetic peptide

<400> SEQUENCE: 49

Leu Tyr Ala Ser Ser Pro Gly Gly Val Tyr Ala Thr Arg Ser Ser
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Synthetic peptide

<400> SEQUENCE: 50

Val Arg Leu Leu Gln Asp Ser Val Asp Phe Ser Ile Leu Ala Asp Ala
1               5                   10                  15

<210> SEQ ID NO 51
```

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 51

Asn Glu Lys Val Glu Leu Gln Glu Leu Asn Asp Arg Phe Ala Asn
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic peptide

<400> SEQUENCE: 52

Gln Asn Lys Ile Leu Leu Ala Glu Leu Glu Gln Leu Lys Gly Gln
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic peptide

<400> SEQUENCE: 53

Glu Glu Met Arg Glu Leu Arg Arg Gln Val Asp Gln Leu Thr Asn
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic peptide

<400> SEQUENCE: 54

Asn Leu Ala Glu Asp Ile Met Arg Leu Arg Glu Lys Leu Gln Glu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic peptide

<400> SEQUENCE: 55

Thr Leu Gln Ser Phe Arg Gln Asp Val Asp Asn Ala Ser Leu Ala
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic peptide

<400> SEQUENCE: 56

Leu Gln Glu Glu Ile Ala Phe Leu Lys Lys Leu His Glu Glu Glu
1               5                   10                  15

<210> SEQ ID NO 57
<211> LENGTH: 15
```

<212> TYPE: PRT
<213> ORGANISM: Artificial Sequence
<220> FEATURE:
<223> OTHER INFORMATION: Synthetic peptide

<400> SEQUENCE: 57

Gln His Val Gln Ile Asp Val Asp Val Ser Lys Pro Asp Leu Thr
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Synthetic peptide

<400> SEQUENCE: 58

Glu Ser Val Ala Ala Lys Asn Leu Gln Glu Ala Glu Glu Trp Tyr
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Synthetic peptide

<400> SEQUENCE: 59

Ala Asn Arg Asn Asn Asp Ala Leu Arg Gln Ala Lys Gln Glu Ser
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic peptide

<400> SEQUENCE: 60

Thr Cys Glu Val Asp Ala Leu Lys Gly Thr Asn Glu Ser Leu Glu
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Synthetic peptide

<400> SEQUENCE: 61

Ala Val Glu Ala Ala Asn Tyr Gln Asp Thr Ile Gly Arg Leu Gln
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: Synthetic peptide

<400> SEQUENCE: 62

Ala Arg His Leu Arg Glu Tyr Gln Asp Leu Leu Asn Val Lys Met
1               5                   10                  15

<210> SEQ ID NO 63
<211> LENGTH: 15
<212> TYPE: PRT

```
<213> ORGANISM: Artificial Sequence
<220> FEATURE:
<223> OTHER INFORMATION: Synthetic peptide

<400> SEQUENCE: 63

Lys Leu Leu Glu Gly Glu Glu Ser Arg Ile Ser Leu Pro Leu Pro
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic peptide

<400> SEQUENCE: 64

Asn Leu Asp Ser Leu Pro Leu Val Asp Thr His Ser Lys Arg Thr
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic peptide

<400> SEQUENCE: 65

Gly Gln Val Ile Asn Glu Thr Ser Gln His His Asp Asp Leu Glu
1               5                   10                  15
```